(12) United States Patent
Anderson et al.

(10) Patent No.: US 8,735,655 B2
(45) Date of Patent: *May 27, 2014

(54) DNA MOLECULES FROM MAIZE AND METHODS OF USE THEREOF

(75) Inventors: Heather M. Anderson, Wildwood, MO (US); Timothy W. Conner, Chesterfield, MO (US); Colleen G. Santino, Sheybogen, WI (US)

(73) Assignee: Monsanto Technology LLC, St. Louis, MO (US)

( * ) Notice: Subject to any disclaimer, the term of this patent is extended or adjusted under 35 U.S.C. 154(b) by 522 days.

This patent is subject to a terminal disclaimer.

(21) Appl. No.: 12/622,354

(22) Filed: Nov. 19, 2009

(65) Prior Publication Data

US 2010/0138963 A1 Jun. 3, 2010

Related U.S. Application Data

(62) Division of application No. 10/213,547, filed on Aug. 6, 2002, now Pat. No. 7,645,919.

(60) Provisional application No. 60/310,370, filed on Aug. 6, 2001.

(51) Int. Cl.
*C12N 15/82* (2006.01)
*C12N 15/10* (2006.01)
*C12N 15/00* (2006.01)
*A01H 5/00* (2006.01)

(52) U.S. Cl.
USPC ........ 800/287; 800/278; 800/295; 435/320.1; 435/468; 536/24.1

(58) Field of Classification Search
None
See application file for complete search history.

(56) References Cited

U.S. PATENT DOCUMENTS

| | | | |
|---|---|---|---|
| 5,652,354 A * | 7/1997 | Mariani et al. | 536/24.1 |
| 5,659,122 A | 8/1997 | Austin | 800/205 |
| 5,919,998 A | 7/1999 | Bandurski et al. | 800/205 |
| 5,962,670 A | 10/1999 | Walling et al. | 800/278 |
| 6,166,293 A * | 12/2000 | Doerner et al. | 800/290 |
| 7,410,800 B2 * | 8/2008 | Bensen et al. | 435/468 |

OTHER PUBLICATIONS

Kim et al 1994, Plant Molecular Biology 24:105-117.*
Benfey et al., "The CaMV 35S enhancer contains at least two domains which can confer different developmental and tissue-specific expression patterns," *EMBO J.*, 8(8):2195-2202, 1989.
Benfey et al., "The cauliflower mosaic virus 35S promoter: combinatorial regulation of transcription in plants," *Science*, 250:959-966, 1990.
Chevalier et al., "Molecular cloning and characterization of six cDNAs expressed during glucose starvation in excised maize (*Zea mays* L.) root tips," *Plant Molecular Biology*, 28:473-485, 1995.
Cho et al., "Regulation of root hair initiation and expansin gene expression in arabidopsis," *The Plant Cell*, 14:3237-3253, 2002.
GenBank Accession No. AF090447, dated Mar. 14, 2003.
GenBank Accession No. AY110698, dated Jun. 13, 2008.
GenBank Accession No. BT034058, dated Jul. 30, 2008.
GenBank Accession No. DQ002406, dated Sep. 6, 2005.
Genbank Accession No. NM_001111392, dated Dec. 14, 2007.
Genbank Accession No. NM_001112034, dated Dec. 14, 2007.
Higuchi et al., "Cloning of nicotianamine synthase genes, novel genes involved in the biosynthesis of phytosiderophores," *Plant Physiol.*, 119:471-480, 1999.
Higuchi et al., "Nicotianamine synthase gene expression differs in barley and rice under Fe-deficient conditions," *The Plant J.*, 25(2):159-167, 2001.
Kahl et al., "Plant genetic engineering for crop improvement," *World J. Microbiol. Biotechnol.*, 11:449-460, 1995.
Kim et al., "A 20 nucleotide upstream element is essential for the nopaline synthase (nos) promoter activity," *Plant Molecular Biology*, 24:105-117, 1994.
Lo et al., "Reduction of light-induced anthocyanin accumulation in inoculated sorghum mesocotyls," *Plant Physiol.*, 116:979-989, 1998.
Odell et al., "Identification of DNA sequences required for activity of the cauliflower mosaic virus 35S promoter," *Nature*, 313:810-812, 1985.
Piechulla et al., "Identification of tomato Lhc promoter regions necessary for circadian expression," *Plant Molecular Biology*, 38:655-662, 1998.
Welsch et al., "Fingerprinting genomes using PCR with arbitrary primers," *Nucleic Acids Res.*, 18(24)7213-7218, 1990.
Welsch et al., "Structural and functional characterization of the phytoene synthase promoter from *Arabidopsis thaliana*," *Planta*, 216:523-534, 2003.

* cited by examiner

*Primary Examiner* — Brent T Page
(74) *Attorney, Agent, or Firm* — Dentons US LLP; Carine M. Doyle, Esq.

(57) ABSTRACT

The present invention relates to DNA polynucleotides for regulating gene expression in plants. In particular, the invention relates to 5' regulatory sequences isolated from *Zea mays* that are useful for regulating gene expression of heterologous DNA molecules in plant roots. The invention also relates to transgenic plants containing the heterologous DNA molecules.

15 Claims, 14 Drawing Sheets

SEQUENCE LISTING

<160> NUMBER OF SEQ ID NOS: 12

<210> SEQ ID NO 1
<211> LENGTH: 23
<212> TYPE: DNA
<213> ORGANISM: Zea mays

<400> SEQUENCE: 1
tcagcgacgg cagcttggcg atg                                          23

<210> SEQ ID NO 2
<211> LENGTH: 38
<212> TYPE: DNA
<213> ORGANISM: Zea mays

<400> SEQUENCE: 2
gcctccatgg tagatctggc tgctacggtt gcagttgg                          38

<210> SEQ ID NO 3
<211> LENGTH: 677
<212> TYPE: DNA
<213> ORGANISM: Zea mays

<400> SEQUENCE: 3
aaatatcgga atattagcat gtcaacttgc actctctaag gctcctttgg aaagcaggat    60
tttagaaaaa aaaatcatat aaatttttta catgaatcag tttatttttcg gattatgaaa  120 tattttctca taacagtata acacatattt tgtatataag ttattatgtt attatatata   180
accgttgcaa cgtacgggca ttcacctagt aaagaaagaa gattaattat tctctggtgg   240
agattgtgcc cgagcccgaa ggtcatgata tggacgttgc aaacccactt cacgagggga   300
caaaaaagaa atagggttac cactttcatc agttaaaggg cgtgacatgg acgtgttgaa   360
gatccggcac attccctgcg aaatatacac gtcatgtac taacgaggca tgaaactggc    420
cacatggcca tggacgcgtg aagcgtgcca tgcattggac atgcggcatc cgaacttctg   480
aagatcatat cagagagaca ctgatgtacg aactgccgta acattctatt ctatatatac   540
cctcagtccc tgttccagtt ctcgttaagc tagcagcacc aagttgtcga acacttgcct   600
gctcttgagc tcgatcaagc tatcatcagc tgcgtcttgc gcacagcaac agcttcccaa   660
ctgcaaccgt agcagcc                                                  677

<210> SEQ ID NO 4
<211> LENGTH: 22
<212> TYPE: DNA
<213> ORGANISM: Artificial Sequence
<220> FEATURE:
<223> OTHER INFORMATION: Adaptor primer 1 (AP1)

<400> SEQUENCE: 4
gtaatacgac tcactatagg gc                                            22

<210> SEQ ID NO 5
<211> LENGTH: 19
<212> TYPE: DNA

```
<213> ORGANISM: Artificial Sequence
<220> FEATURE:
<223> OTHER INFORMATION: Adaptor primer 2 (AP2)

<400> SEQUENCE: 5
actatagggc acgcgtcct                                                    19

<210> SEQ ID NO 6
<211> LENGTH: 20
<212> TYPE: DNA
<213> ORGANISM: Zea mays

<400> SEQUENCE: 6
gccgcacttg cagcttgagc                                                   20

<210> SEQ ID NO 7
<211> LENGTH: 41
<212> TYPE: DNA
<213> ORGANISM: Zea mays

<400> SEQUENCE: 7
gatcgatccc atggtagatc ttgtggtgct aaagaagctc g                           41

<210> SEQ ID NO 8
<211> LENGTH: 1027
<212> TYPE: DNA
<213> ORGANISM: Zea mays

<400> SEQUENCE: 8
cctccatata tgattgtcgt cgggcccata acagcatctc ctccaccagt ttattgtaag         60
aataaattaa gtagagatat ttgtcgtcgg gcagaagaaa cttggacaag aagaagaagc        120
aagctaggcc aatttcttgc cggcaacagg aagatagtgg cctctagttt atatatcggc        180
gtgatgatga tgctcctagc tagaaatgag agaagaaaaa cggacgcgtg tttggtgtgt        240
gtcaatggcg tccatccttc catcagatca gaacgatgaa aaagtcaagc acggcatgca        300
tagtatatgt atagcttgtt ttagtgtggc tttgctgaga cgaatgaaag caacggcggg        360 catattttc agtggctgta gctttcaggc tgaaagagac gtggcatgca ataattcagg         420
gaattcgtca gccaattgag gtagctagtc aacttgtaca ttggtgcgag caattttccg        480
cactcaggag ggctagtttg agagtccaaa aactatagga gattaaagag ctaaaatcc         540 tctccttatt taattttaaa taagtagtgt atttgtattt taactcctcc aacccttccg        600
attttatggc tctcaaacta gcattcagtc taatgcatgc atgcttggct agaggtcgta        660
tggggttgtt aatagcatag ctagctacaa gttaaccggg tcttttatat ttaataagga        720
caggcaaagt attacttata aataaagaat aaagctagga cgaactggat tactaaatcg        780
aaatggacgt aatattccag gcaagaataa ttcttcgatc aggagacaag tggggcattg        840
gaccggttct tgcaagcaag agcctatggc gtggtgccac ggcgcgttgc ccatacatca        900
tgcctccatc gatgatccat cctcacttgc tataaaaaga ggtgtccatg gtgctcaagc        960
tcagccaagc aaataagacg acttgtttca ttgattcttc aagagatcga gcttctttag       1020
caccaca                                                                 1027

<210> SEQ ID NO 9
<211> LENGTH: 24
<212> TYPE: DNA
<213> ORGANISM: Zea mays

<400> SEQUENCE: 9
```

```
tgggaggcga ccttgggcgc cagg                                         24
```

<210> SEQ ID NO 10
<211> LENGTH: 35
<212> TYPE: DNA
<213> ORGANISM: Zea mays

<400> SEQUENCE: 10

```
tcggaggcca tggtagatct agtgatcgat cggcc                             35
```

<210> SEQ ID NO 11
<211> LENGTH: 748
<212> TYPE: DNA
<213> ORGANISM: Zea mays

<400> SEQUENCE: 11

```
cgatcagtct aagaatgacc agaagcaaca acgacttcag acctttagac catgacatct    60
agaagaaggt atatgcaagc aaaatacatc taaagcatct gactgactcg ttagtgctag   120
cccttcttct gaacaacttc tttctaagta tatgaataag aaggtcgttt cacacaattg   180
atcgacaaaa cgatcaatat catccacaac gaggaagcaa tccatgcaag ggcaaaagcc   240
gaataaatcg gcccaggaag tggtgcaacc aatgtcgcct actcatccgc tctaggaatg   300
tcgtgttact ttccaccagt ctactcatcg atgatgtttt atcctgctaa catgtgaaaa   360
agtatgacga tgaatccgta ttacacaggg gcggacgcag agggaggcaa agtgggtcat   420
agccacctca attttcatga tattttatat atcatgacgt gcagtctctt tgcaaccccca  480
gccacattaa ttaatagact ccaccgacga gcgacgagtg atggtaccgg ccgccggccc   540
aggccaaccc aagtggaaaa ggccgacgac tcccggacgt ctcatcctca ccggacgcca   600
ccaaccccccg caatctccag acgtacgagc cgcctattta aagccctcag tctgccactc   660
tcatggcaac gcaagcagaa gctacaatcc taaaaccatc tgcttcagcc ttcagctagc    720
cccaagttta gtcggccgat cgatcact                                      748
```

<210> SEQ ID NO 12
<211> LENGTH: 298
<212> TYPE: DNA
<213> ORGANISM: Zea mays

<400> SEQUENCE: 12

```
gcaccaagtt gtcgatcact tgcctgctct tgagctcgat caagctatca tcagctacag    60
cttccgatcc caactgcaac tgtagcagcg acaactgcca tggaggccca gaacgtggag   120
gttgctgccc tggtgcagaa gatcacggcc ctccacgccg acatcgccaa gctgccgtcg   180
ctgagcccgt cccccgacgc caacgcgctg ttcaccagcc tcgtcatggc ctgcgtcccg   240
ccaaaccctg tcgacgtgac caagctcagc ccggacgtcc aggggatgcg agaggagc    298
```

DNA MOLECULES FROM MAIZE AND METHODS OF USE THEREOF

This application is a divisional of U.S. application Ser. No. 10/213,547, filed Aug. 6, 2002 now U.S. Pat. No. 7,645,919, the disclosure of which is incorporated herein by reference in its entirety, which application claims the benefit of priority of U.S. Provisional application No. 60/310,370, filed Aug. 6, 2001.

FIELD OF THE INVENTION

The present invention relates to the isolation and use of nucleic acid molecules for control of gene expression in plants. Specifically a novel DNA molecule isolated from *Zea mays* and its use to express transgene products in plants. The methods of the present invention provide for the isolation of novel DNA molecules that have promoter function for enhanced expression in root tissues of transgenic plants.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al. (1995) World Journal of Microbiology and Biotechnology 11:449-460). Particularly desirable traits or qualities of interest for plant genetic engineering would include, but are not limited to, resistance to insects and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes from a heterologous source, or a native source, but modified to have different or improved qualities, and incorporate the exogenous DNA into the plant's genome. The gene or gene(s) can then be expressed in the plant cell to exhibit the added characteristic(s) or trait(s). In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

Isolated plant promoters are useful for modifying plants through genetic engineering to have desired phenotypic characteristics. In order to produce such a transgenic plant, a vector that includes a heterologous gene sequence that confers the desired phenotype when expressed in the plant is introduced into the plant cell. The vector also includes a plant promoter that is operably linked to the heterologous gene sequence, often a promoter not normally associated with the heterologous gene. The vector is then introduced into a plant cell to produce a transformed plant cell, and the transformed plant cell is regenerated into a transgenic plant. The promoter controls expression of the introduced DNA sequence to which the promoter is operably linked and thus affects the desired characteristic conferred by the DNA sequence.

Since the promoter is a 5' regulatory element that plays an integral part in the overall expression of a gene or gene(s), it would be advantageous to have a variety of promoters to tailor gene expression such that a gene or gene(s) is transcribed efficiently at the right time during plant growth and development, in the optimal location in the plant, and in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli, or in a particular plant tissue or organ. The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant, that each gene is modulated or controlled for optimal expression and that the regulatory elements are diverse, to reduce the potential of gene silencing that can be caused by recombination of homologous sequences. In light of these and other considerations, it is apparent that optimal control of gene expression and regulatory element diversity are important in plant biotechnology.

The proper regulatory sequences must be present and in the proper location with respect to the DNA sequence of interest, for the newly inserted DNA to be transcribed and thereby, if desired, translated into a protein in the plant cell. These regulatory sequences include but are not limited to a promoter, a 5' untranslated leader, and a 3' polyadenylation sequence. The ability to select the tissues in which to transcribe such foreign DNA, and the time during plant growth in which to obtain transcription of such foreign DNA is also possible through the choice of appropriate promoter sequences that control transcription of these genes.

A variety of different types or classes of promoters can be used for plant genetic engineering. Promoters can be classified on the basis of range or tissue specificity. For example, promoters referred to as constitutive promoters are capable of transcribing operatively linked DNA sequences efficiently and expressing said DNA sequences in multiple tissues. Tissue-enhanced or tissue-specific promoters can be found upstream and operatively linked to DNA sequences normally transcribed in higher levels in certain plant tissues or specifically in certain plant tissues. This can be referred to as differential expression when expression levels are compared relative to other plant cells or tissues. Other classes of promoters would include but are not limited to inducible promoters that can be triggered by external stimuli such as chemical agents, developmental stimuli, or environmental stimuli. Thus, the different types of promoters desired can be obtained by isolating the upstream 5' regulatory regions of DNA sequences that are transcribed and expressed in a constitutive, tissue-enhanced, or inducible manner.

The technological advances of high-throughput sequencing and bioinformatics has provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced and the expressed sequences catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue enhanced sequence can then be used as a probe or primer to clone the corresponding full-length cDNA. A genomic library of the target plant can then be used to isolate the corresponding gene and the associated regulatory elements, including promoter sequences.

Multiple promoter sequences that confer a desired expression profile such as promoters capable of regulating expression of operably linked genes in multiple tissues can be isolated by selectively comparing cDNA libraries of target tissues of interest with non-target or background cDNA libraries to find the 5' regulatory regions associated with the expressed sequences in those target libraries. The isolated promoter sequences can be used for selectively modulating expression of any operatively linked gene and provide additional regulatory element diversity in a plant expression vector in gene stacking approaches.

SUMMARY OF THE INVENTION

The present invention provides nucleic acid molecules comprising a DNA polynucleotide sequence set forth in SEQ ID NO:3 or any fragments, regions, cis elements or homologue of the sequence that are capable of regulating transcription of operably linked DNA sequences.

Another aspect of the present invention relates to the use of at least one fragment, region, or cis element thereof of SEQ ID NO:3 that can be combined to create novel promoter DNA sequences or used in a novel combination with another heterologous regulatory sequence to create a hybrid or chimeric promoter capable of modulating transcription of an operably linked DNA sequence.

Hence, the present invention relates to the use of a DNA polynucleotide disclosed in SEQ ID NO:3, or any fragment, region, cis elements or homologue of the disclosed molecules that are capable of regulating transcription of an operably linked DNA sequence. Therefore, the invention not only encompasses the DNA polynucleotide as disclosed in SEQ ID NO:3, but also includes any truncated or deletion derivatives, or fragments or regions thereof that are capable of functioning independently as a plant promoter including cis elements that are capable of functioning as regulatory sequences in conjunction with one or more regulatory sequences when operably linked to a transcribable sequence.

The present invention thus encompasses a novel plant promoter or a hybrid or chimeric promoter that functions in plants to cause RNA transcription comprising a DNA polynucleotide of SEQ ID NO3. The hybrid or chimeric promoters can consist of any length fragments, regions, or cis elements of the disclosed DNA polynucleotide of SEQ ID NO:3 combined with any other transcriptionally active minimal or full-length promoter. For example, a fragment of the DNA polynucleotide set forth in SEQ ID NO:3 may be combined with a plant DNA virus promoter or other promoter sequences or cis elements identified therein to construct a novel hybrid promoter. More preferably, the DNA polynucleotide set forth in SEQ IN NO:3 or fragments thereof, may be combined with promoters or fragments of promoters that function to direct enhanced transcription of an operably linked DNA molecule into plant root cells and tissues.

A DNA polynucleotide fragment of SEQ ID NO:3 from position 110-192 and DNA polynucleotide fragments at least 90% homologous to this sequence is an aspect of the present invention. A DNA polynucleotide fragment of SEQ ID NO:3 from position 126-164 and DNA polynucleotide fragments at least 90% homologous to this sequence is an aspect of the present invention.

The present invention also encompasses DNA molecules that comprise plant expression constructs containing the disclosed DNA polynucleotide set forth in SEQ ID NO:3 or any fragments, regions, cis elements or homologue thereof, including novel promoters generated using the disclosed DNA sequences or any fragment, region, or cis element of the disclosed DNA sequences operably linked to a heterologous DNA polynucleotide comprising a gene of interest, operably linked to a 3' termination polynucleotide sequence.

The present invention also includes any transgenic plant cells and transgenic plants containing the DNA molecule comprising a plant expression construct containing the DNA polynucleotide set forth in SEQ ID NO:3, or any fragments, regions, cis elements or homologue thereof in operable linkage to a heterologous DNA polynucleotide sequence.

The present invention also provides a DNA molecule for enhancing transcription of a linked DNA molecule preferably in plant root cells and root tissues by linking a heterologous gene of interest DNA molecule to the DNA polynucleotide set forth in SEQ ED NO:3 or any fragment, region, cis element or homologue thereof, and a 3' termination polynucleotide sequence The present invention also provides a transgenic plant made by a method comprising: a) constructing a plant expression construct comprising (i) a DNA polynucleotide comprising the DNA sequence set forth in SEQ ID NO:3, or fragments, regions, cis elements or homologue thereof, operably linked to, (ii) a transcribable heterologous DNA sequence and (iii) a 3' termination polynucleotide sequence, b) transforming a plant cell with the plant expression construct, and c) regenerating the transformed plant cell into a fertile plant.

The DNA polynucleotide set forth in SEQ ID NO:3 or fragments thereof, can be used in a method of isolating DNA polynucleotides, wherein SEQ ID NO:3 or fragments thereof can be used as probes or primer molecules to isolate similar DNA polynucleotides that function as promoters to enhance transcription of a linked gene of interest in plant root cells or root tissues.

The DNA polynucleotide set forth in SEQ ID NO:12 or fragments thereof, can be used in a method of isolating DNA polynucleotides, wherein SEQ ID NO:12 or fragments thereof can be used as probes or primer molecules to isolate associated DNA polynucleotides that function as promoters to enhance transcription of a linked gene of interest in plant root cells or root tissues. The DNA polynucleotides isolated by the method, wherein the DNA polynucleotides are isolated from monocot plants and function as promoters that enhance expression of a heterologous gene sequence in plant root cells and root tissues.

A DNA promoter polynucleotide can be isolated by a method comprising the steps of: (i) preparation of plant genomic DNA; and (ii) preparation of a mixture of degenerate DNA polynucleotide primers to a length of the translation product of SEQ ID NO:12; and (iii) mixing said degenerate DNA polynucleotide primers and genomic DNA with a second DNA polynucleotide primer not homologous to SEQ ID NO:12; and (iv) subjecting said mixture to a PCR condition that provides an amplicon; and (v) purifying said amplicon; (vi) inserting said amplicon into an expression construct; and (vii) testing said expression construct for expression of a reporter molecule.

The foregoing and other aspects of the invention will become more apparent from the following detailed description and accompanying drawings.

DETAILED DESCRIPTION OF THE INVENTION

Definitions and Methods

Figure 1:
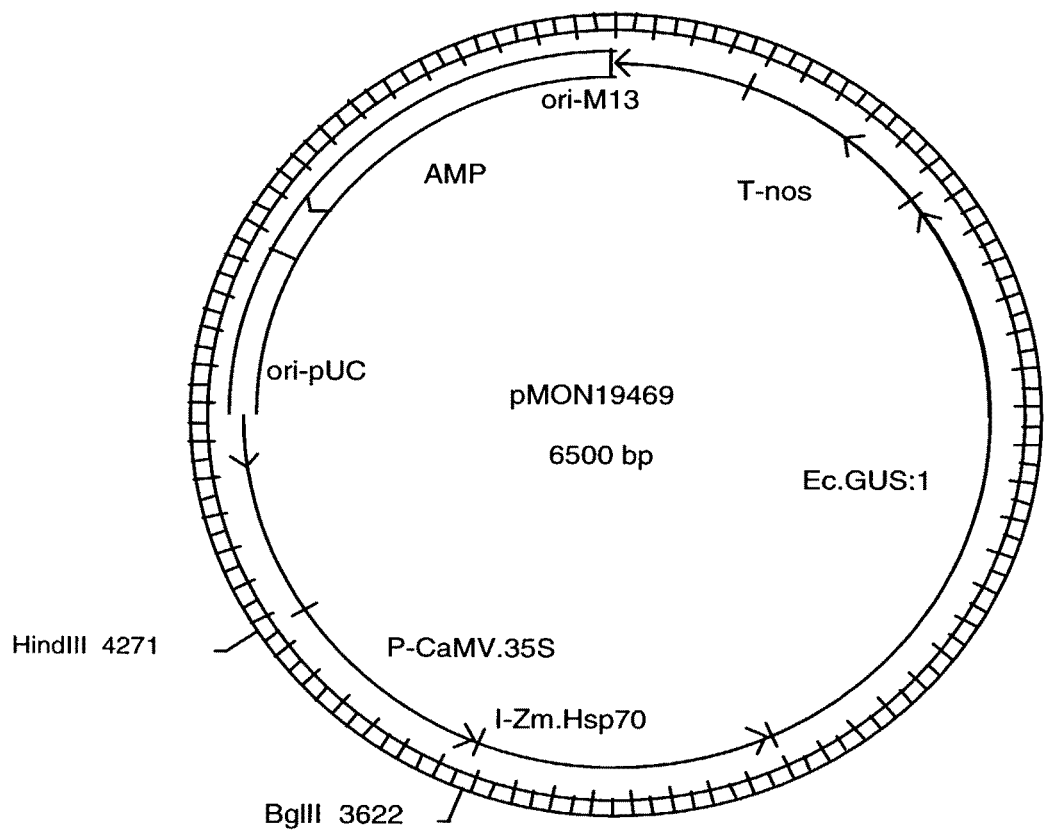
FIG. 1 is a plasmid map of pMON19469

The following definitions and methods are provided to better define the present invention and to guide those of ordinary skill in the art in the practice of the present invention. Unless otherwise noted, terms are to be understood according to conventional usage by those of ordinary skill in the relevant art. The nomenclature for DNA bases as set forth at 37 CFR §1.822 is used. The standard one- and three-letter nomenclature for amino acid residues is used.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" refers to a DNA sequence that originates from a different species. Heterologous can also mean being different from where it exists in nature, such as from a different place in the genome as in a different member of a gene family, or a different allele of the same gene or if from the same source, is modified from its original form.

An "isolated" nucleic acid sequence or isolated DNA polynucleotide is substantially separated or purified away from other nucleic acid sequences with that the nucleic acid is normally associated in the cell of the organism in which the nucleic acid naturally occurs, i.e., other chromosomal or extrachromosomal DNA. The term embraces nucleic acids and polynucleotides that are biochemically purified so as to substantially remove contaminating nucleic acids and other cellular components. The term also embraces recombinant nucleic acids and chemically synthesized polynucleotides.

The term "substantially purified, as used herein, refers to a molecule separated from substantially all other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" does not encompass molecules present in their native state.

A first nucleic acid sequence displays "substantial identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman Adv. Appl. Math. 2:482, 1981; by the homology alignment algorithm of Needleman and Wunsch, J. Mol. Biol. 48:443, 1970; by the search for similarity method of Pearson and Lipman, Proc. Natl. Acad. Sci. USA 85:2444, 1988; preferably by computerized implementations of these algorithms (GAP, BESTFIT, FASTA, and TFASTA in the Wisconsin Genetics Software Package Release 7.0, Genetics Computer Group, 575 Science Dr., Madison, Wis. The reference nucleic acid may be a full-length molecule or a portion of a longer molecule. Alternatively, two nucleic acids are have substantial identity if one hybridizes to the other under stringent conditions, as defined below.

A first polynucleotide sequence is "operably linked" with a second polynucleotide sequence when the sequences are so arranged that the first polynucleotide sequence affects the function of the second polynucleotide sequence. Preferably, the two sequences are part of a single contiguous nucleic acid molecule and more preferably are adjacent. For example, a promoter is operably linked to a gene of interest if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Sambrook et al., Molecular Cloning, A Laboratory Manual, 2nd Ed., Cold Spring Harbor Press, Cold Spring Harbor, N.Y., 1989, herein referred to as Sambrook et al., 1989, and Ausubel et al., 1992).

Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers.

An "artificial polynucleotide sequence" can be designed and chemically synthesized for enhanced expression in particular host cells and for the purposes of cloning into appropriate vectors. Computer programs are available for these purposes including, but not limited to the "BestFit" or "Gap" programs of the Sequence Analysis Software Package, Genetics Computer Group, Inc., University of Wisconsin Biotechnology Center, Madison, Wis. 53711.

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence that is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into messenger RNA (mRNA) then translated into polypeptides (structural genes); other genes can be transcribed into other types of RNA (e.g. rRNA, tRNA, antisense RNA); and these other types of RNAs can function as regulators of expression.

"Expression" of a gene refers to the transcription of a gene to produce the corresponding mRNA. This mRNA may be translated to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to promoter regions, 5' untranslated leaders, introns, genes, 3' untranslated regions, and other regulatory sequences or sequences that affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Bacterial, fungal, plant, animal are often used to describe the construct or vector, for example, "plant expression cassette" includes all of the genetic elements known to those skilled in the art of plant molecular biology that permit the expression product to be produced in plant cells.

"Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins, e.g., promoters that have similar function may have homologous cis elements. Polynucleotides are homologous when under certain conditions they specifically hybridize to form a duplex molecule. A DNA molecule can have substantial identity with another DNA molecule, if the sequence of polynucleotides is homologous or complementary under specified conditions. Under these specified conditions, referred to as stringency conditions, one DNA molecule can be used as a probe or primer to identify other DNA molecules that share homology. Homology can also be determined by computer programs that align polynucleotide sequences and estimate the ability of DNA molecules to form duplex molecules under certain stringency conditions. A length of polynucleotide sequence can be related to another polynucleotide sequence by the number of identical nucleotides of the length, this is referred to as percent homology. DNA molecules from different sources that share a high degree of homology are referred to as "homologues".

"ESTs" or Expressed Sequence Tags are short sequences of randomly selected clones from a cDNA (or complementary DNA) library that are representative of the cDNA inserts of these randomly selected clones (McCombie, et al., Nature Genetics, 1:124, 1992; Kurata, et al., Nature Genetics, 8: 365,1994; Okubo, et al., Nature Genetics, 2: 173, 1992).

The term "electronic Northern" refers to a computer-based sequence analysis that allows sequences from multiple cDNA libraries to be compared electronically based on parameters the researcher identifies including abundance in EST populations in multiple cDNA libraries, or exclusively to EST sets from one or combinations of libraries.

"Subsetting" refers to any method of comparing nucleic acid sequences from different or multiple sources that can be used to identify the profile of the nucleic acid sequences that reflects gene transcription activity and message stability in a particular tissue, at a particular time, or under particular conditions.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Any plant promoter can be used as a 5' regulatory sequence for modulation expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, that is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50:349-383, 1981; Messing et al., In: Genetic Engineering of Plants, Kosuge et al., eds., pp. 211-227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211-227, 1983). In addition, virtually all promoters include additional upstream activating sequences or enhancers (Benoist and Chambon, Nature 290:304-310, 1981; Gruss et al., Proc. Nat. Acad. Sci. USA 78:943-947, 1981; to and Khoury and Gruss, Cell 27:313-314, 1983) extending from around −100 by to −1,000 by or more upstream of the transcription initiation site.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991). Alternatively, heterologous regulatory sequences can be added to the 5' upstream region of an inactive, truncated promoter, e.g., a promoter including only the core TATA and, sometimes, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Promoters are typically comprised of multiple distinct "cis-acting transcriptional regulatory elements," or simply "cis-elements," each of which appears to confer a different aspect of the overall control of gene expression (Strittmatter et al., Proc. Nat. Acad. Sci. USA 84:8986-8990, 1987; Ellis et al., EMBO J. 6:11-16, 1987; Benfey et al., EMBO J. 9:1677-1684, 1990). "cis elements" bind trans-acting protein factors that regulate transcription. Some cis elements bind more than one factor, and trans-acting transcription factors may interact with different affinities with more than one cis element (Johnson and McKnight, Ann. Rev. Biochem. 58:799-839, 1989). Plant transcription factors, corresponding cis elements, and analysis of their interaction are discussed, for example, in: Martin, Curr. Opinions Biotech. 7:130-138, 1996; Murai, In: Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300. The promoter sequences of the present invention can contain "cis elements" that can confer or modulate gene expression.

Cis elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by sequence similarity with known cis element motifs by conventional sequence comparison methods. The fine structure of a cis element can be further studies by mutagenesis (or substitution) of one or more nucleotides or by other conventional methods. See, e.g., Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300.

Cis elements can be obtained by chemical synthesis or by cloning from promoters that includes such elements, and they can be synthesized with additional flanking sequences that contain useful restriction enzyme sites to facilitate subsequence manipulation. In one embodiment, the promoters are comprised of multiple distinct "cis-acting transcriptional regulatory elements," or simply "cis-elements," each of which appears to confer a different aspect of the overall control of gene expression (Strittmatter et al., Proc. Nat. Acad. Sci. USA 84:8986-8990, 1987; Ellis et al., EMBO J. 6:11-16, 1987; Benfey et al., EMBO J. 9:1677-1684, 1990). In a preferred embodiment sequence regions comprising "cis elements" of the nucleic acid sequences of SEQ ID NO:3 are identified using computer programs designed specifically to identify cis elements, or domains or motifs within sequences.

The present invention includes cis elements of SEQ ID NO:3 or homologues of cis elements known to effect gene regulation that show homology with the nucleic acid sequences of the present invention. A number of such elements are known in the literature, such as elements that are regulated by numerous factors such as light, heat, or stress; elements that are regulated or induced by pathogens or chemicals, and the like. Such elements may either positively or negatively regulated gene expression, depending on the conditions. Examples of cis elements would include but are not limited to oxygen responsive elements (Cowen et al., J. Biol. Chem. 268(36):26904, 1993), light regulatory elements (see for example, Bruce and Quaill, Plant Cell 2(11): 1081. 1990, and Bruce et al., EMBO J. 10:3015, 1991, a cis element reponsive to methyl jasmonate treatment (Beaudoin and Rothstein, Plant Mol. Biol. 33:835, 1997, salicylic acid responsive elements (Strange et al., Plant J. 11:1315, 1997, heat shock response elements (Pelham et al., Trends Genet. 1:31, 1985, elements responsive to wounding and abiotic stress (Loace et al., Proc. Natl. Acad. Sci. U.S.A. 89:9230, 1992; Mhiri et al., Plant Mol. Biol. 33:257, 1997), low temperature elements (Baker et al., Plant Mol. Biol. 24:701, 1994; Jiang et al., Plant Mol. Biol. 30:679, 1996; Nordin et al., Plant Mol. Biol. 21:641, 1993; Zhou et al., J. Biol. Chem. 267:23515, 1992), and drought responsive elements, (Yamaguchi et al., Plant Cell 6:251-264, 1994; Wang et al., Plant Mol. Biol. 28:605, 1995; Bray E. A. Trends in Plant Science 2:48, 1997).

The present invention therefore encompasses "cis elements" or "motifs" of the disclosed polynucleotide sequence and the region of the disclosed sequence that comprises the motifs. The polynucleotide regions of the present invention are less than the full length of the sequence encompassed by SEQ ID NO:3, and can contain one or more regulatory elements including but not limited to cis elements or motifs that are capable of enhancing transcription of operably linked DNA sequences in plant root cells and tissues.

Plant promoters can include promoters produced through the manipulation of known promoters to produce synthetic, chimeric, or hybrid promoters. Such promoters can also combine cis elements from one or more promoters, for example, by adding a heterologous regulatory sequence to an active promoter with its own partial or complete regulatory sequences (Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant. Mol. Biol. 15:373-381, 1991). Chimeric promoters have also been developed by adding a heterologous regulatory sequence to the 5' upstream region of an inactive, truncated promoter, i.e., a promoter that includes only the core TATA and, optionally, the CCAAT elements (Fluhr et al., Science 232:1106-1112, 1986; Strittmatter and Chua, Proc. Nat. Acad. Sci. USA 84:8986-8990, 1987; Aryan et al., Mol. Gen. Genet. 225:65-71, 1991). The design, construction, and use of chimeric or hybrid promoters comprising at least one cis element of SEQ ID NO:3 for modulating the expression of operably linked nucleic acid sequences is also encompassed by the present invention.

The promoter sequences, fragments, regions or cis elements thereof of SEQ ID NO:3 are capable of transcribing operably linked DNA sequences in multiple tissues and can selectively regulate expression of genes in these tissues. For a number of agronomic traits, expression of a gene or genes of interest is desirable in multiple tissues in order to confer the desired characteristic(s). The availability of suitable promoters that regulate transcription of operably linked genes in selected target tissues of interest is important since it may not be desirable to have expression in every tissue, but only in certain tissues. For example, if one desires to control an insect pest that targets particular tissues, it would be of interest to express the desired gene product(s) in those tissues. For herbicide tolerance, it may be desirable to have a promoter that transcribes operably linked genes in a manner that confers herbicide tolerance at the desired levels in both vegetative and reproductive tissues. Consequently, it is important to have a wide variety of choices of 5' regulatory elements for any plant biotechnology strategy. Herbicides that are incorporated into the soil and function as preemergence herbicides function by inhibition the emerging root or hypocotyl. A root enhanced promoter linked to a preemergence resistance gene that functions in the emerging root is useful in a method to enhance crop tolerance to these preemergence herbicides.

The advent of genomics, which comprises molecular and bioinformatics techniques, has resulted in rapid sequencing and analyses of a large number of DNA samples from a vast number of targets, including but not limited to plant species of agronomic importance. To identify the nucleic acid sequences of the present invention from a database or collection of cDNA sequences, the first step involves constructing cDNA libraries from specific plant tissue targets of interest. Briefly, the cDNA libraries are first constructed from these tissues that are harvested at a particular developmental stage, or under particular environmental conditions. By identifying differentially expressed genes in plant tissues at different developmental stages, or under different conditions, the corresponding regulatory sequences of those genes can be identified and isolated. Transcript imaging enables the identification of tissue-preferred sequences based on specific imaging of nucleic acid sequences from a cDNA library. By transcript imaging as used herein is meant an analysis that compares the abundance of expressed genes in one or more libraries. The clones contained within a cDNA library are sequenced and the sequences compared with sequences from publicly available databases. Computer-based methods allows the researcher to provide queries that compare sequences from multiple libraries. The process enables quick identification of clones of interest compared with conventional hybridization subtraction methods known to those of skill in the art.

Using conventional methodologies, cDNA libraries can be constructed from the mRNA of a given tissue or organism using poly dT primers and reverse transcriptase (Efstratiadis, et al., Cell 7:279, 1976; Higuchi, et al., Proc. Natl. Acad. Sci. (U.S.A.) 73:3146, 1976; Maniatis, et al., Cell 8:163, 1976; Land et al., Nucleic Acids Res. 9:2251, 1981; Okayama, et al., Mol. Cell. Biol. 2:161, 1982; Gubler, et al., Gene 25:263, 1983).

Several methods can be employed to obtain full-length cDNA constructs. For example, terminal transferase can be used to add homopolymeric tails of dC residues to the free 3' hydroxyl groups (Land, et al., Nucleic Acids Res. 9:2251, 1981). This tail can then be hybridized by a poly dG oligo that can act as a primer for the synthesis of full length second strand cDNA. Okayama and Berg, report a method for obtaining full length cDNA constructs. This method has been simplified by using synthetic primer-adapters that have both homopolymeric tails for priming the synthesis of the first and second strands and restriction sites for cloning into plasmids (Coleclough, et al., Gene 34:305, 1985) and bacteriophage vectors (Krawinkel, et al., Nucleic Acids Res. 14:1913, 1986; and Han, et al., Nucleic Acids Res. 15:6304, 1987).

These strategies can be coupled with additional strategies for isolating rare mRNA populations. For example, a typical mammalian cell contains between 10,000 and 30,000 different mRNA sequences. Davidson, Gene Activity in Early Development, 2nd ed., Academic Press, New York, 1976. The number of clones required to achieve a given probability that a low-abundance mRNA will be present in a cDNA library is $N=(\ln(1-P))/(\ln(1-1/n))$ where N is the number of clones required, P is the probability desired, and 1/n is the fractional proportion of the total mRNA that is represented by a single rare mRNA (Sambrook, et al., 1989).

One method to enrich preparations of mRNA for sequences of interest is to fractionate by size. One such method is to fractionate by electrophoresis through an agarose gel (Pennica, et al., Nature 301:214, 1983). Another such method employs sucrose gradient centrifugation in the presence of an agent, such as methylmercuric hydroxide, that denatures secondary structure in RNA (Schweinfest, et al., Proc. Natl. Acad. Sci. (U.S.A.) 79:4997-5000, 1982).

A frequently adopted method is to construct equalized or normalized cDNA libraries (Ko, Nucleic Acids Res. 18:5705, 1990; Patanjali, S. R. et al., Proc. Natl. Acad. Sci. (U.S.A.) 88:1943, 1991). Typically, the cDNA population is normalized by subtractive hybridization. Schmid, et al., J. Neurochem. 48:307, 1987; Fargnoli, et al., Anal. Biochem. 187:364, 1990; Travis, et al., Proc. Natl. Acad. Sci. (U.S.A.) 85:1696, 1988; Kato, Eur. J. Neurosci. 2:704, 1990; and Schweinfest, et al., Genet. Anal. Tech. Appl. 7:64, 1990). Subtraction represents another method for reducing the population of certain sequences in the cDNA library (Swaroop, et al., Nucleic Acids Res. 19:1954, 1991). Normalized libraries can be constructed using the Soares procedure (Soares et al., Proc. Natl. Acad. Sci. (U.S.A.) 91:9228, 1994). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected, and clones for rare transcripts are effectively increased in abundance.

ESTs can be sequenced by a number of methods. Two basic methods can be used for DNA sequencing, the chain termination method of Sanger et al., Proc. Natl. Acad. Sci. (U.S.A.) 74: 5463, 1977 and the chemical degradation method of Maxam and Gilbert, Proc. Nat. Acad. Sci. (U.S.A.) 74: 560, 1977. Automation and advances in technology such as the replacement of radioisotopes with fluorescence-based sequencing have reduced the effort required to sequence DNA (Craxton, Methods, 2: 20, 1991; Ju et al., Proc. Natl. Acad. Sci. (U.S.A.) 92: 4347, 1995; Tabor and Richardson, Proc. Natl. Acad. Sci. (U.S.A.) 92: 6339, 1995). Automated sequencers are available from a number of manufacturers, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

ESTs longer than 150 by have been found to be useful for similarity searches and mapping. (Adams, et al., Science 252:1651, 1991. EST sequences normally range from 150-450 bases. This is the length of sequence information that is routinely and reliably generated using single run sequence data. Typically, only single run sequence data is obtained from the cDNA library, Adams, et al., Science 252:1651, 1991. Automated single run sequencing typically results in an approximately 2-3% error or base ambiguity rate. (Boguski, et al., Nature Genetics, 4:332, 1993).

EST databases have been constructed or partially constructed from, for example, *C. elegans* (McCombrie, et al., Nature Genetics 1:124, 1992, human liver cell line HepG2 (Okubo, et al., Nature Genetics 2:173,1992); human brain RNA (Adams, et al., Science 252:1651, 1991; Adams, et al., Nature 355:632, 1992); *Arabidopsis*, (Newman, et al., Plant Physiol. 106:1241, 1994); and rice (Kurata, et al., Nature Genetics 8:365, 1994). The present invention uses ESTs from a number of libraries prepared from corn root and leaf tissues as a tool for the identification of genes expressed in these tissues, which then facilitates the isolation of 5' regulatory sequences such as promoters that regulate the genes.

Computer-based sequence analyses can be used to identify differentially expressed sequences including but not limited to those sequences expressed in one tissue compared with another tissue. For example, a different set of sequences can be found from cDNA isolated from plant tissue isolated from root tissue versus leaf tissue. Accordingly, sequences can be compared from cDNA libraries prepared from plants grown under different environmental or physiological conditions. Once the preferred sequences are identified from the cDNA library of interest, the genomic clones can be isolated from a genomic library prepared from the plant tissue, and corresponding regulatory sequences including but not limited to 5' regulatory sequences can be identified and isolated.

In one preferred embodiment, expressed sequence tags (EST) sequences from a variety of cDNA libraries are catalogued in a sequence database. This database is used to identify promoter targets from a particular tissue of interest. The selection of expressed sequence tags for subsequent promoter isolation is reflective of the presence of one or more sequences among the representative ESTs from a random sampling of an individual cDNA library, or a collection of cDNA libraries. For example, the identification of regulatory sequences that regulate the expression of transcripts in leaf and root tissue is conducted by identifying ESTs found in leaf and root cDNA libraries and absent or in lower abundance in other cDNA libraries and the expression profile for a given EST is assessed. By abundance as used herein is meant the number of times a clone or cluster of clones appears in a library. The sequences that are enhanced or in high abundance in a specific tissue or organ that represent a target expression profile are identified in this manner and primers can be designed from the identified EST sequences. A PCR-based approach can be used to amplify flanking regions from a genomic library of the target plant of interest. A number of methods are known to those of skill in the art to amplify unknown DNA sequences adjacent to a core region of known sequence. Methods include but are not to limited to inverse PCR (IPCR), vectorette PCR, Y-shaped PCR and genome walking approaches.

In a preferred embodiment, genomic DNA ligated to an adapter is subjected to a primary round of PCR amplification with a gene-specific primer and a primer that anneals to the adapter sequence. The PCR product is next used as the template for a nested round of PCR amplification with a second gene-specific primer and second adapter. The resulting fragments from the nested PCR reaction are then isolated, purified and subcloned into an appropriate vector. The fragments are sequenced and the translational start sites can be identified when the EST is derived from a truncated cDNA. The fragments can be cloned into plant expression vectors as transcriptional or translational fusions with a reporter gene such as β-glucuronidase (GUS). The constructs can be tested in transient analyses and subsequently the 5' regulatory regions are operably linked to other genes and regulatory sequences of interest in a suitable plant transformation vector and the transformed plants are analyzed for the expression of the gene(s) of interest by any number of methods known to those of skill in the art.

Any plant can be selected for the identification of genes and regulatory sequences. Examples of suitable plant targets for the isolation of genes and regulatory sequences would include but are not limited to Acadia, alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castor-bean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plant targets would include corn, cotton, soybean, and wheat.

The nucleic acid molecules of the present invention are isolated from corn (*Zea mays*). The corn plant develops about 20-21 leaves, silks about 65 days post-emergence, and matures about 125 days post-emergence. Normal corn plants follow a general pattern of development, but the time interval between different stages and morphology varies between different hybrids, growth and environmental conditions.

There are a number of identifiable stages in corn plant development. The stages are defined as vegetative (V) and reproductive (R) stages. Subdivisions of the V stages are numerically designated as V1, V2, V3, etc., through V(n) where (n) represents the last leaf stage before tasseling (VT) and the first V stage is the emergence (VE) stage. For example, VE is the emergence from the soil of a seedling leaf, V1 represents the first true leaf, V2 represents the second leaf, etc. The reproductive stages include the first appearance of silk to the mature seed and are represented as follows: R1 is silking, R2 is blistering, R3 is the milk stage, R4 is the dough stage, R5 is the dent stage, and R6 is physiological maturity (see for example, Ritchie S W et al. (1986) How a Corn Plant Develops, Iowa State University of Science and Technology Cooperative Exension Service, Ames, Iowa 48: 1-21).

Any method that allows a differential comparison between different types or classes of sequences can be used to isolate genes or regulatory sequences of interest. For example in one differential screening approach, a cDNA library from mRNA isolated from a particular tissue can be prepared in a bacteriophage host using a commercially available cloning kit. The plaques are spread onto plates containing a lawn of a bacterial host such as *E. coli* to generate bacteriophage plaques. About $10^5$-$10^6$ plaques can be lifted onto DNA binding membranes. Duplicate membranes are probed using probes generated from mRNA from the target and non-target or background tissue. The probes are labeled to facilitate detection after hybridization and development. Plaques that hybridize to target tissue-derived probes but not to non-target tissue derived probes that display a desired differential pattern of expression can be selected for further analysis. Genomic DNA libraries can also be prepared from a chosen species by partial digestion with a restriction enzyme and size selecting the DNA fragments within a particular size range. The genomic DNA can be cloned into a suitable vector including but not limited to a bacteriophage, and prepared using a suitable kit as described earlier (see for example, Stratagene, La Jolla, Calif. or Gibco BRL, Gaithersburg, Md.).

Differential hybridization techniques as described are well known to those of skill in the art and can be used to isolate a desired class of sequences. By classes of sequences as used herein is meant sequences that can be grouped based on a common identifier including but not limited to sequences isolated from a common target plant, a common library, or a common plant tissue type. In a preferred embodiment, sequences of interest are identified based on sequence analyses and querying of a collection of diverse cDNA sequences from libraries of different tissue types.

A number of methods used to assess gene expression are based on measuring the mRNA level in an organ, tissue, or cell sample. Typical methods include but are not limited to RNA blots, ribonuclease protection assays and RT-PCR. In another preferred embodiment, a high-throughput method is used whereby regulatory sequences are identified from a transcript profiling approach. The development of cDNA microarray technology enables the systematic monitoring of gene expression profiles for thousands of genes (Schena et al, Science, 270: 467, 1995). This DNA chip-based technology arrays thousands of cDNA sequences on a support surface. These arrays are simultaneously hybridized to a-multiple of labeled cDNA probes prepared from RNA samples of different cell or tissue types, allowing direct comparative analysis of expression. This technology is first demonstrated by analyzing 48 *Arabidopsis* genes for differential expression in roots and shoots (Schena et al, Science, 270:467, 1995). More recently, the expression profiles of over 1400 genes are monitored using cDNA microarrays (Ruan et al, The Plant Journal 15:821, 1998). Microarrays provide a high-throughput, quantitative and reproducible method to analyze gene expression and characterize gene function. The transcript profiling approach using microarrays thus provides another valuable tool for the isolation of regulatory sequences such as promoters associated with those genes.

The present invention uses high throughput sequence analyses to form the foundation of rapid computer-based identification of sequences of interest. Those of skill in the art are aware of the resources available for sequence analyses. Sequence comparisons can be undertaken by determining the similarity of the test or query sequence with sequences in publicly available or proprietary databases ("similarity analysis") or by searching for certain motifs ("intrinsic sequence analysis") (e.g. cis elements) (Coulson, Trends in Biotechnology, 12:76, 1994; Birren, et al., Genome Analysis, 1:543, 1997).

The nucleotide sequences provided in SEQ ID NO:3 or fragments thereof, or complements thereof, or a nucleotide sequence at least 90% substantial identity, preferably 95% substantial identity even more preferably 99% or 100% substantial identity to the sequence provided in SEQ ID NO:3 or fragment thereof, or cis element thereof, or complement of the sequence thereof, can be "provided" in a variety of mediums to facilitate use. Such a medium can also provide a subset thereof in a form that allows one of skill in the art to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising computer readable medium having recorded thereon a nucleotide sequence of the present invention.

By providing one or more of nucleotide sequences of the present invention, those of skill in the art can routinely access the sequence information for a variety of purposes. Computer software is publicly available that allows one of skill in the art to access sequence information provided in a computer readable medium. Examples of public databases would include but are not limited to the DNA Database of Japan (DDJB) (www.ddbj.nig.ac.jp); Genbank (www.ncbi.nlm.nih.gov/web/Genbank/Index.html); and the European Molecular Biology Laboratory Nucleic Acid Sequence Database (EMBL) (www.ebi.ac.uk/ebi_docs/embl_db.html) or versions thereof. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology, 12:76-80, 1994; Birren et al., Genome Analysis, 1:543, 1997).

Any program designed for motif searching also has utility in the present invention. Sequence analysis programs designed for motif searching can be used for identification of cis elements. Preferred computer programs would include but are not limited to MEME, SIGNAL SCAN, and GENESCAN. Meme is a program that identifies conserved motifs (either nucleic acid or peptide) in a group of unaligned sequences. Meme saves these motifs as a set of profiles. These profiles can be used to search a database of sequences. A MEME algorithm (version 2.2) can be found in version 10.0 of the GCG package; MEME (T. Bailey and C. Elkan, Machine Learning, 21(1-2):51-80,1995) and the location of the website is as follows: (www.sdsc.edu/MEME/meme/website/COPYRIGHT.html.). Signal_Scan is a program that identifies known motifs in the test sequences using information from other motif databases (Prestridge, D.S., CABIOS 7, 203-206 (1991)). Signal_Scan version 4.0 information is available at the following website: biosci.cbs.umn.cdu/software/sigscan.html. The ftp site for Signal Scan is biosci.cbs.umn.edu/software/sigscan.html. Databases used with Signal Scan include PLACE (www.dna.affrc.go.ip/htdocs/PLACE (Higo et al., Nucleic Acids Research 27(1):297-300 (1999)) and TRANSFAC (Heinemeye, X. et al., Nucleic Acid Research 27(1):318-322) that can be found at the following website: transfac.gbf.de/. GeneScan is another suitable program for motif searching (Burge, C. and Karlin, S. J., Mol. Biol. 268, 78-94 (1997)) and version 1.0 information is available at the following website: gnomic-.stanford.edu/GENESCANW.html. As used herein, "a target structural motif", or "target motif" refers to any rationally selected sequence or combination of sequences in which the sequence(s) are chosen based on a three-dimensional configuration that is formed upon the folding of the target motif. There are a variety of target motifs known to those of skill in the art. Protein target motifs include, but are not limited to, enzymatic active sites and signal sequences. Preferred target motifs of the present invention would include but are not limited to promoter sequences, cis elements, hairpin structures and other expression elements such as protein binding sequences.

As used herein, "search means" refers to one or more programs that are implemented on the computer-based system to compare a target sequence or target structural motif with the sequence information stored within the data storage means. Search means are used to identify fragments or regions of the sequences of the present invention that match a particular target sequence or target motif. Also, multiple sequences can be compared in order to identify common regions or motifs that may be responsible for specific functions. For example, cis elements or sequence domains that confer a specific expression profile can be identified when multiple to promoter regions of similar classes of promoters are aligned and analyzed by certain software packages.

The present invention further provides systems, particularly computer-based systems, which contain the sequence information described herein. As used herein, a "computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. Those of skill in the art can appreciate that any one of the available computer-based systems are suitable for use in the present invention.

DNA molecules for use as PCR primers are designed from the cDNA sequences identified from the computer-based sequence comparisons. These sequences are used to extend the nucleic acid sequence using polymerase chain reaction (PCR) amplification techniques (see for example, Mullis et al., Cold Spring Harbor Symp. Quant. Biol. 51:263, 1986; Erlich, et al., European Patent Appln. 50,424; European Patent Appln. 84,796, European Patent Appln. 258,017, European Patent Appln. 237,362; Mullis, European Patent Appln. 201,184; Mullis, et al., U.S. Pat. No. 4,683,202; Erlich, U.S. Pat. No. 4,582,788; and Saiki, et al., U.S. Pat. No. 4,683,194). A number of PCR amplification methods are known to those of skill in the art, and are used to identify nucleic acid sequences adjacent to a known sequence. For example, inverse PCR (IPCR) methods to amplify unknown DNA sequences adjacent to a core region of known sequence have been described. Other methods are also available such as capture PCR (Lagerstrom M., et al., PCR Methods Applic. 1:111, 1991, and walking PCR (Parker, J D et al., Nucl. Acids Res 19:3055, 1991). A number of manufacturers have also developed kits based on modifications of these methods for the purposes of identifying sequences of interest. Technical advances including improvements in primer and adapter design, improvements in the polymerase enzyme, and thermocycler capabilities have facilitated quicker, efficient methods for isolating sequences of interest.

In a preferred embodiment, the flanking sequences containing the 5' regulatory elements of the present invention are isolated using a genome-walking approach (Universal GenomeWalker™ Kit, CLONTECH Laboratories, Inc., Palo, Alto, Calif.). In brief, the purified genomic DNA is subjected to a restriction enzyme digest that produces genomic DNA fragments with ends that are ligated with GenomeWalker™ adapters. GenomeWalker™ primers are used along with gene specific primers in two consecutive PCR reactions (primary and nested PCR reactions) to produce PCR products containing the 5' regulatory sequences that are subsequently cloned and sequenced.

In addition to their use in modulating gene expression, the promoter sequences of the present invention also have utility as probes or primers in nucleic acid hybridization experiments. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa, Nucl. Acids Res. 12:203-213, 1984; and Wetmur and Davidson, J. Mol. Biol. 31:349-370, 1968. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results.

The nucleic acid sequences in SEQ ID NO:3 and any variants thereof, are capable of hybridizing to other nucleic acid sequences under appropriately selected conditions of stringency. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low stringency" conditions. Similarly, the molecules are said to be "complementary" is they can hybridize to one another with sufficient stability to permit them to remain annealed to one another under conventional "high stringency" conditions. Conventional stringency conditions are described by Sambrook, et al., Molecular Cloning, A Laboratory Manual, 2nd Ed., Cold Spring Harbor Press, Cold Spring Harbor, N.Y., 1989, and by Haymes et al., Nucleic Acid Hybridization, A Practical Approach, IRL Press, Washington, D.C., 1985.

In a preferred embodiment, the nucleic acid sequences, SEQ ID NO:3, or a fragment, region, cis element, or oligomer of any of these sequences, may be used in hybridization assays of other plant tissues to identify closely related or homologous genes and associated regulatory sequences. These include but are not limited to Southern hybridization assays on any substrate including but not limited to an appropriately prepared plant tissue, cellulose, nylon, or combination filter, chip, or glass slide. Such methodologies are well known in the art and are available in a kit or preparation that can be supplied by commercial vendors.

Of course, fragments can also be obtained by other techniques such as by directly synthesizing the fragment by chemical means, as is commonly practiced by using an automated oligonucleotide synthesizer. Also, fragments can be obtained by application of nucleic acid reproduction technology, such as the PCR™ (polymerase chain reaction) technology by recombinant DNA techniques generally known to those of skill in the art of molecular biology. Regarding the amplification of a target nucleic-acid sequence (e.g., by PCR) using a particular amplification primer pair, "stringent PCR conditions" refer to conditions that permit the primer pair to hybridize only to the target nucleic-acid sequence to which a primer having the corresponding wild-type sequence (or its complement) would bind and preferably to produce a unique amplification product.

A fragment comprises at least a minimum length of identical polynucleotide sequence. The fragment can be used in hybridization or PCR under stringent hybridization conditions as defined above to isolate like molecules. For example, for the present invention a fragment length of polynucleotide sequence is one that would have polynucleotide sequence identical to at least 36 nucleotides of SEQ ID NO:3.

The nucleic acid sequences of the present invention can also be used as probes and primers. Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions and hybridize specifically to a target native sequence of another species under lower stringency conditions. Preferably, probes and primers according to the present invention have complete sequence similarity with the native sequence, although probes differing from the native sequence and that retain the ability to hybridize to target native sequences may be designed by conventional methods. Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (herein referred to as, "Ausubel et al., 1992"); and Innis et al., PCR Protocols: A Guide to Methods and Applications, Academic Press: San Diego, 1990, herein incorporated by reference in their entirety. PCR-primer pairs can be derived from a known sequence, for example, by using computer programs intended for that purpose such as Primer (Version 0.5, © 1991, Whitehead Institute for Biomedical Research, Cambridge, Mass.). Primers and probes based on the native promoter sequences disclosed herein can be used to confirm and, if necessary, to modify the disclosed sequences by conventional methods, e.g., by re-cloning and re-sequencing.

In another embodiment, the nucleotide sequence of the promoter disclosed herein can be modified. Those skilled in the art can create DNA molecules that have variations in the nucleotide sequence. The nucleotide sequence of the present invention as shown in SEQ ID NO:3 may be modified or altered to enhance their control characteristics. One preferred method of alteration of a nucleic acid sequence is to use PCR to modify selected nucleotides or regions of sequences. These methods are known to those of skill in the art. Sequences can be modified, for example by insertion, deletion or replacement of template sequences in a PCR-based DNA modification approach. "Variant" DNA molecules are DNA molecules containing changes in which one or more nucleotides of a native sequence is deleted, added, and/or substituted, preferably while substantially maintaining promoter function. In the case of a promoter fragment, "variant" DNA can include changes affecting the transcription of a minimal promoter to which it is operably linked. Variant DNA molecules can be produced, for example, by standard DNA mutagenesis techniques or by chemically synthesizing the variant DNA molecule or a portion thereof.

In another embodiment, the nucleotide sequences as shown in SEQ ID NO:3 includes any length of said nucleotide sequences that is capable of regulating an operably linked DNA sequence. For example, the sequences as disclosed in SEQ ID NO:3 may be truncated or portions deleted and still be capable of regulating transcription of an operably linked DNA sequence. In a related embodiment, a cis element of the disclosed sequences may confer a particular specificity such as conferring enhanced expression of operably linked DNA sequences in certain tissues and therefore is also capable of regulating transcription of operably linked DNA sequences. Consequently, any sequence fragments, portions, or regions of the disclosed sequences of SEQ ID NO:3 can be used as regulatory sequences, including but not limited to cis elements or motifs of the disclosed sequences. For example, one or more base pairs may be deleted from the 5' or 3' end of a promoter sequence to produce a "truncated" promoter. One or more base pairs can also be inserted, deleted, or substituted internally to a promoter sequence. Promoters can be constructed such that promoter fragments or elements are operably linked, for example, by placing such a fragment upstream of a minimal promoter. A minimal or basal promoter is a piece of DNA that is capable of recruiting and binding the basal transcription machinery. One example of basal transcription machinery in eukaryotic cells is the RNA polymerase II complex and its accessory proteins. The enzymatic components of the basal transcription machinery are capable of initiating and elongating transcription of a given gene, utilizing a minimal or basal promoter. That is, there are not added cis-acting sequences in the promoter region that are capable of recruiting and binding transcription factors that modulate transcription, e.g., enhance, repress, render transcription hormone-dependent, etc. Substitutions, deletions, insertions or any combination thereof can be combined to produce a final construct.

Native or synthetic nucleic acids according to the present invention can be incorporated into recombinant nucleic acid constructs, typically DNA constructs, capable of introduction into and replication in a host cell. In one preferred embodiment, the nucleotide sequences of the present invention as shown in SEQ ID NO:3 or fragments, variants, or derivatives thereof are incorporated into an expression vector cassette that includes the promoter regions of the present invention operably linked to a genetic component such as a selectable, screenable, or scorable marker gene. The disclosed nucleic acid sequences of the present invention are preferably operably linked to a genetic component such as a nucleic acid that confers a desirable characteristic associated with plant morphology, physiology, growth and development, yield, nutritional enhancement, disease or pest resistance, or environmental or chemical tolerance. These genetic components such as marker genes or agronomic genes of interest can function in the identification of a transformed plant cell or plant, or a produce a product of agronomic utility.

In a preferred embodiment, one genetic component produces a product that serves as a selection device and functions in a regenerable plant tissue to produce a compound that would confer upon the plant tissue resistance to an otherwise toxic compound. Genes of interest for use as a selectable, screenable, or scorable marker gene would include but are not limited to the coding sequence for β-glucuronidase (GUS), the coding sequence for green fluorescent protein (GFP), the coding sequence for luciferase (LUX), antibiotic, or herbicide tolerance genes. Examples of transposons and associated antibiotic resistance genes include the transposons Tns (bla), Tn5 (nptII), Tn7 (dhfr), penicillins, kanamycin (and neomycin, G418, bleomycin); methotrexate (and trimethoprim); chloramphenicol; kanamycin and tetracycline.

Characteristics useful for selectable markers in plants have been outlined in a report on the use of microorganisms (Advisory Committee on Novel Foods and Processes, July 1994). These include stringent selection with minimum number of nontransformed tissues, large numbers of independent transformation events with no significant interference with the regeneration, application to a large number of species, and availability of an assay to score the tissues for presence of the marker.

A number of selectable marker genes are known in the art and several antibiotic resistance markers satisfy these criteria, including those resistant to kanamycin (nptII), hygromycin B (aph IV), streptomycin or spectinomycin (aad, spec/strep) and gentamycin (aac3 and aacC4). Useful dominant selectable marker genes include genes encoding antibiotic resistance genes, e.g., resistance to hygromycin, kanamycin, bleomycin, G418, streptomycin or spectinomycin; and herbicide resistance genes (e.g., phosphinothricin acetyltransferase, mutant ALS, class II EPSPS and modified class I EPSPS). A useful strategy for selection of transformants for herbicide resistance is described, e.g., in Vasil, Cell Culture and Somatic Cell Genetics of Plants, Vols. I-III, Laboratory Procedures and Their Applications Academic Press, New York, 1984. Particularly preferred selectable marker genes for use in the present invention would genes that confer resistance to compounds such as antibiotics like kanamycin, and herbicides like glyphosate (Della-Cioppa et al., Bio/Technology 5(6), 1987, U.S. Pat. Nos. 5,463,175, 5,633,435). Other selection devices can also be implemented and would still fall within the scope of the present invention.

For the practice of the present invention, conventional compositions and methods for preparing and using vectors and host cells are employed, as discussed, inter alia, in Sambrook et al., 1989). In a preferred embodiment, the host cell is a plant cell. A number of vectors suitable for stable transfection of plant cells or for the establishment of transgenic plants have been described in, e.g., Pouwels et al., Cloning Vectors: A Laboratory Manual, 1985, supp. 1987); Weissbach and Weissbach, Methods for Plant Molecular Biology, Academic Press, 1989; Gelvin et al., Plant Molecular Biology Manual, Kluwer Academic Publishers, 1990; and R. R. D. Croy, Plant Molecular Biology LabFax, BIOS Scientific Publishers, 1993. Plant expression vectors can include, for example, one or more cloned plant genes under the transcriptional control of 5' and 3' regulatory sequences. They can also can include a selectable marker as described to allow selection of host cells containing the expression vector. Such plant expression vectors also typically contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and a polyadenylation signal. Other sequences, of bacterial origin are also included to allow the vector to be cloned in a bacterial host. The vector will also typically contain a broad host range prokaryotic origin of replication. In a particularly preferred embodiment, the host cell is a plant cell and the plant expression vector comprises a promoter region as disclosed in SEQ ID NO:3, an operably linked transcribable sequence, and a transcription termination sequence. Other regulatory sequences can also be included such as 5' non-translated leaders, in addition to restriction enzyme sites for cloning purposes.

Promoters have utility for plant gene expression for any gene of interest including but not limited to selectable markers, scorable markers, genes for pest tolerance, disease tolerance, herbicide tolerance, nutritional enhancements and any other gene, coding sequence or noncoding sequence of agronomic interest. Examples of constitutive promoters useful for plant gene expression include, but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988) and the octopine synthase promoter (Fromm et al., Plant Cell 1:977, 1989) and the figwort mosaic virus (FMV) promoter (U.S. Pat. No. 6,018,100).

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize RbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, or Safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989).

The promoter of the present invention is a plant promoter that is capable of transcribing operatively linked DNA sequences in multiple plant tissues, however, preferably expression is enhanced in root cells and root tissues relative to other plant cells and tissues.

Plant expression vectors can include RNA processing signals, e.g., introns, which may be positioned upstream or downstream of a polypeptide-encoding sequence in the transgene. In addition, the expression vectors may include additional regulatory sequences from the 3'-untranslated region (3' UTR) of plant genes (Thornburg et al., Proc. Natl. Acad. Sci. USA 84:744 (1987); An et al., Plant Cell 1:115 (1989), e.g., a 3' UTR to increase mRNA stability of the mRNA, such as the PI-II termination region of potato or the octopine or nopaline synthase 3' termination regions). 5' untranslated regions (5'UTR) of a mRNA can play an important role in translation initiation and can also be a genetic component in a plant expression vector. For example, non-translated 5' leader sequences derived from heat shock protein genes have been demonstrated to enhance gene expression in plants (see, for example U.S. Pat. No. 5,362,865 herein incorporated by reference in its entirety). These additional upstream and downstream regulatory sequences may be derived from a source that is native or heterologous with respect to the other elements present on the expression vector.

The promoter sequence of the present invention is used to control gene expression in plant cells. The disclosed promoter sequence comprises genetic components that are part of DNA constructs used in plant transformation. The promoter sequences of the present invention can be used with any suitable plant transformation plasmid or vector containing a selectable or screenable marker and associated regulatory elements, as described, along with one or more nucleic acids expressed in a manner sufficient to confer a particular desirable trait. Examples of suitable structural genes of agronomic interest envisioned by the present invention would include but are not limited to one or more genes for insect tolerance, such as *Bacillus thuringiensis* insecticidal protein genes, disease tolerance such as genes for fungal disease control, bacterial disease control and nematode control, herbicide tolerance e.g., genes conferring glyphosate tolerance, phosphinothricine tolerance, ALS inhibitor tolerance, atrazine tolerance, acteoclor tolerance, alaclor tolerance, metoalaclor tolerance, isoxaflutole tolerance, and genes for quality improvements such as yield, nutritional enhancements, environmental or stress tolerances (e.g. drought, nutrient, heat, cold, pollution) or any desirable changes in plant physiology, growth, development, morphology or plant product(s).

Alternatively, the DNA coding sequences can effect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207, 1991). The RNA could also be a catalytic RNA molecule (i.e., a ribozyme) engineered to cleave a desired endogenous mRNA product (see for example, Gibson and Shillitoe, Mol. Biotech. 7:125, 1997). Thus, any gene that produces a protein or mRNA that expresses a phenotype or morphology change of interest are useful for the practice of the present invention.

In addition to regulatory elements or sequences located upstream (5') or within a DNA sequence, there are downstream (3') sequences that affect gene expression and thus the term regulatory sequence as used herein refers to any nucleotide sequence located upstream, within, or downstream to a DNA sequence that controls, mediates, or affects expression of a gene product in conjunction with the protein synthetic apparatus of the cell.

The promoter sequences of the present invention may be modified, for example for expression in other plant systems. In another approach, novel hybrid promoters can be designed or engineered by a number of methods. Many promoters contain upstream sequences that activate, enhance or define the strength and/or specificity of the promoter (Atchison, Ann. Rev. Cell Biol. 4:127, 1988). T-DNA genes, for example contain "TATA" boxes defining the site of transcription initiation and other upstream elements located upstream of the transcription initiation site modulate transcription levels (Gelvin, In Transgenic Plants (Kung, S.-D. And Us, R., eds), San Diego: Academic Press, pp. 49-87, 1988). Another chimeric promoter combined a trimer of the octopine synthase (ocs) activator to the mannopine synthase (mas) activator plus promoter and reported an increase in expression of a reporter gene (Min Ni et al., The Plant Journal 7:661, 1995). The upstream regulatory sequences of the present invention can be used for the construction of such chimeric or hybrid promoters. Methods for construction of variant promoters of the present invention include, but are not limited to, combining control elements of different promoters or duplicating portions or regions of a promoter (see for example, U.S. Pat. Nos. 4,990,607, 5,110,732, and 5,097,025, herein incorporated by reference in their entirety). Those of skill in the art are familiar with the standard resource materials that describe specific conditions and procedures for the construction, manipulation and isolation of macromolecules (e.g., DNA molecules, plasmids, etc.), generation of recombinant organisms and the screening and isolation of genes, (see for example Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: volume 1, Analyzing DNA, (1997); volume 2, Detecting Genes, (1998); volume 3, Cloning Systems, (1999), volume 4, Mapping Genomes, (1999), Cold Spring Harbor, N.Y.).

The promoter sequences of the present invention can be incorporated into an expression vector using screenable or scorable markers as described and tested in transient analyses that provide an indication of gene expression in stable plant systems. Methods of testing gene expression in transient assays are known to those of skill in the art. Transient expression of marker genes has been reported using a variety of plants, tissues and DNA delivery systems. For example, types of transient analyses can include but are not limited to direct gene delivery via electroporation or particle bombardment of tissues in any transient plant assay using any plant species of interest. Such transient systems would include but are not limited to protoplasts from suspension cultures in wheat (Zhou et al., Plant Cell Reports 12:612, 1993), electroporation of leaf protoplasts of wheat (Sethi et al., J. Crop Sci. 152, 1983); electroporation of protoplast prepared from corn tissue (Sheen, J., Plant Cell 3: 225, 1991), or particle bombardment of specific tissues of interest. The present invention encompasses the use of any transient expression system to evaluate regulatory sequences operatively linked to selected reporter genes, marker genes or agronomic genes of interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker can be used in a transient assay. Preferred marker genes for transient analyses of the promoters or 5' regulatory sequences of the present invention include a GUS gene (coding sequence for β-glucuronidase) or a GFP gene (coding sequence for green fluorescent protein). The expression vectors containing the 5' regulatory sequences operably linked to a marker gene are delivered to the tissues and the tissues are analyzed by the appropriate mechanism, depending on the marker. The quantitative or qualitative analyses are used as a tool to evaluate the potential expression profile of the 5' regulatory sequences when operatively linked to genes of agronomic interest in stable plants. Ultimately, the promoter sequences of the present invention are directly incorporated into suitable plant transformation expression vectors comprising the 5' regulatory sequences operatively linked to selectable markers and genes of interest, transformed into plants and the plants analyzed for the desired expression profile conferred by the 5' regulatory sequences.

Those of skill in the art are aware of the vectors and suitable for plant transformation. Suitable vectors would include but are not limited to disarmed Ti-plasmids for *Agrobacterium*-mediated methods. These vectors can contain a resistance marker, 1 or more T-DNA borders, or 1 or more T-DNAs and origins of replication for *E. coli* and *Agrobacterium* along with one or more genes of interest and associated regulatory regions. Those of skill in the art are aware that for *Agrobacterium*-mediated approaches a number of strains and methods are available. Such strains would include but are not limited to *Agrobacterium* strains C58, LBA4404, EHA101 and EHA105. Particularly preferred strains are *Agrobacterium tumefaciens* strains. Other DNA delivery systems for plant transformation are also known to those of skill in the art and include but is not limited to particle bombardment of selected plant tissues.

Exemplary nucleic acids that may be introduced by the methods encompassed by the present invention include, for example, DNA sequences or genes from another species, or even genes or sequences that originate with or are present in the same species, but are incorporated into recipient cells by genetic engineering methods rather than classical reproduction or breeding techniques. However, the term exogenous, is also intended to refer to genes that are not normally present in the cell being transformed, or perhaps simply not present in the form, structure, etc., as found in the transforming DNA segment or gene, or genes that are normally present yet that one desires, e.g., to have over-expressed. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

The plant transformation vectors containing the promoter sequences of the present invention may be introduced into plants by any plant transformation method. Several methods are available for introducing DNA sequences into plant cells and are well known in the art. Suitable methods include but are not limited to bacterial infection, binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include, but are not limited to, cotton (U.S. Pat. Nos. 5,004,863, 5,159,135; 5,518,908, WO 97/43430), soybean (U.S. Pat. Nos. 5,569,834; 5,416,011; McCabe et al., Bio/Technology, 6:923, 1988; Christou et al., Plant Physiol., 87:671, 1988); *Brassica* (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including, but not limited to, asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes, C. A., et al., Science, 240: 204, 1988; Gordon-Kamm, et al., Plant Cell, 2: 603, 1990; Fromm, et al., Bio/Technology, 8: 833, 1990; Koziel, et al., Bio/Technology, 11: 194, 1993); oats (*Avena sativa*; Somers, et al., Bio/Technology, 10: 1589, 1992); orchardgrass (*Dactylis glomerata*; Horn, et al., Plant Cell Rep., 7: 469, 1988); rice (*Oryza sativa*, including indica and japonica varieties, Toriyama, et al., Bio/Technology, 6: 10, 1988; Zhang, et al., Plant Cell Rep., 7: 379, 1988; Luo and Wu, Plant Mol. Biol. Rep., 6: 165, 1988; Zhang and Wu, Theor. Appl. Genet., 76: 835, 1988; Christou, et al., Bio/Technology, 9: 957, 1991); sorghum (*Sorghum bicolor*; Casas, A. M., et al., Proc. Natl. Acad. Sci. U.S.A., 90: 11212, 1993); sugar cane (*Saccharum* spp.; Bower and Birch, Plant J., 2: 409, 1992); tall fescue (*Festuca arundinacea*; Wang, Z. Y. et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks T., et al., Plant Physiol., 102: 1077, 1993; Becker, et al., Plant, J. 5: 299, 1994), and alfalfa (Masoud, S. A., et al., Transgen. Res., 5: 313, 1996). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoter sequences of the present invention. Those of skill in the art are aware of the numerous methods available for the analysis of transformed plants. A variety of methods are used to assess gene expression and determine if the introduced gene(s) is integrated, functioning properly, and inherited as expected. For the present invention the promoters can be evaluated by determining the expression levels of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

The methods of the present invention including, but not limited to cDNA library preparation, genomic library preparation, sequencing, sequence analyses, PCR technologies, vector construction, transient assays, and plant transformation methods are well known to those of skill in the art and are carried out using standard techniques or modifications thereof.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Plant Material, DNA Isolation and cDNA Library Construction

A number of tissues and plant developmental stages are selected for preparation of the corn libraries. Those of skill in the art are aware of the variations in tissue selection and preparation that occur from one tissue sampler to the next. The following are the conditions for the target libraries:

Seeds are planted at a depth of about 3 cm in soil into 2"-3" pots containing Metro Mix 200 growing medium and transplanted into larger 10" pots containing the same soil after 2-3 weeks. Peters 15-16-17 fertilizer is applied about 3 times per week after transplanting, at a strength of 150 ppm N 2-3 times during the life of the plant from transplanting to flowering. A total of about 900 mg Fe is added to each pot. Corn plants are grown in the greenhouse in 15 hr day/9 hr night cycles. The daytime temperature is 80° F. and the night temperature is 70° F. Lighting is provided by 1000 W sodium vapor lamps.

Tissue Isolation.

A root cDNA library is generated from corn (*Zea mays*) root tissue at the V8 plant developmental stage. The root tissue is collected when the corn plant is at the 8-leaf stage. The root system is cut from the plant and rinsed with water to remove the soil. The tissue is frozen in liquid nitrogen and the harvested tissue is stored at −80° C. until the RNA is prepared. cDNA synthesis is initiated using a NotI-oligo(dT) primer. Double-stranded cDNA is blunted, ligated to SalI adaptors, digested with NotI, size-selected, and cloned into the NotI and SalI sites of the pSPORT vector (LTI). cDNA synthesis is initiated using a NotI-oligo(dT) primer. Double-stranded cDNA is blunted, ligated to EcoRI adaptors, digested with NotI, size-selected, and cloned into the NotI and EcoRI sites of the pINCY vector (Incyte Genomics, Palo Alto, Calif.).

The corn undeveloped leaf cDNA library is generated from young corn plants. The tissue is collected when the corn plant is at a 6-leaf developmental stage. The second youngest leaf that is at the base of the apical leaf of the V6 corn plant is cut at the base and immediately transferred to liquid nitrogen containers and the leaves are crushed. The harvested tissue is stored at −80° C. until the RNA is prepared.

For preparation of the cDNA libraries, the RNA is purified using Trizol reagent available from Life Technologies (Gaithersburg, Md.) essentially as recommended by the manufacturer. Poly A+ RNA (mRNA) is purified using magnetic oligo dT beads essentially as recommended by the manufacturer (Dynabeads, Dynal Corporation, Lake Success, N.Y.).

Construction of cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md.) is used, following the conditions suggested by the manufacturer.

The cDNA libraries are plated on LB agar containing the appropriate antibiotics for selection and incubated at 37° C. for a sufficient time to allow the growth of individual colonies. Single colonies are individually placed in each well of a 96-well microtiter plate containing LB liquid including selective antibiotics. The plates are incubated overnight at approximately 37° C. with gentle shaking to promote growth of the cultures. The plasmid DNA is isolated from each clone using Qiaprep Plasmid Isolation kits, using the conditions recommended by the manufacturer (Qiagen Inc., Santa Clara, Calif.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif.).

Example 2

Promoter Identification

A database of EST sequences derived from the cDNA libraries prepared from various corn tissues is used to identify the promoter candidates for expression of operably linked DNA sequences in multiple tissues. The sequences are also used as query sequences against GenBank databases that contain previously identified and annotated sequences and searched for regions of homology using BLAST programs. For example, the translation product of the EST sequence (Zm.700102320EST, SEQ ID NO:12) starting at position 100 of SEQ ID NO:12 shows homology to nicotianamine synthase from *Hordeum vulgare* (Higuchi et al., 1999. Plant Physiol. 119:471-480, herein incorporated by reference in its entirety) and *Oryza sativa* (Higuchi et al., 2001. Plant J. 25:159-167, herein incorporated by reference in its entirety). The translation of the EST sequence is used to identify the P-Zm.700203408 genomic DNA fragment from *Zea mays* and this polynucleotide has homology to metallothionein from *Zea mays* (Chevalier et al. 1995. Plant Mol Biol 28:473-485), and the translation of the EST sequence is used to identify the P-Zm.700204518 genomic DNA fragment from *Zea mays* and this polynucleotide has homology to the pathogenesis-related protein from *Sorghum bicolor* (Lo et al. 1998. Plant Physiol. 116:979-989). The selection of expressed sequence tags (ESTs) for subsequent promoter isolation is based on the presence of one or more sequences among the representative ESTs from a random sampling of an individual cDNA library or collection of cDNA libraries. The Zm.700102320EST is used to identify a genomic DNA fragment from *Zea mays* that is the promoter polynucleotide of the present invention, P-Zm.700102320.

cDNA libraries can be made from any plant species. Those of skill in the art can use the Zm.700102320EST sequence of the present invention (SEQ ID NO:12) to design a mixture of synthetic polynucleotides of degenerate DNA polynucleotide sequence to the translation product of the Zm.700102320EST for use as primers or probes to identify and isolate associated DNA molecules from a plant genomic DNA library, e.g., genomic DNA libraries made from DNA isolated from rice (*Oryza sativa*), barley (*Hordeum vulgare*), corn (*Zea mays*) or from any plant species. These primers in combination with a random primer can be used to produce an amplicon in a PCR method from corn or heterologous genomic DNA libraries. The amplicon can be inserted into a plant expression construct and tested for the capability to enhance transgene expression in root cells.

Example 3

Genomic Library Construction, PCR Amplification and Promoter Isolation

For a genomic library, corn DNA from maize hybrid (Fr27rhm X FrMo17rhm, Illinois Foundation Seed Co.) is isolated by a CsCl purification protocol according to Ausubel et al., 1992, by a CTAB purification method (Rogers et al., Plant Mol. Biol., 5:69, 1988) or a similar DNA isolation method suitable for the isolation of plant DNA. Reagents are available commercially (see, for example Sigma Chemical Co., St. Louis, Mo.). The libraries are prepared according to manufacturer instructions (GENOME WALKER, a trademark of CLONTECH Laboratories, Inc, Palo Alto, Calif.). In separate reactions, genomic DNA is subjected to restriction enzyme digestion overnight at 37° C. with the following blunt-end endonucleases: EcoRV, Scat, DraI, PvuII, or StuI (CLONTECH Laboratories, Inc. Palo Alto, Calif.). The reaction mixtures are extracted with phenol:chloroform, ethanol precipitated, and resuspended in Tris-EDTA buffer. The purified blunt-ended genomic DNA fragments are then ligated to the GenomeWalker™ adaptors and ligation of the resulting DNA fragments to adaptors are done according to manufacturer protocol. The GenomeWalker™ sublibraries are aliquoted and stored at −20° C.

Genomic DNA ligated to the GenomeWalker™ adaptor from the genomic library is subjected to PCR amplification in separate reactions with gene-specific primers (GSP1) of the primary reaction, GSP1.HH (SEQ ID NO:1) and adaptor primer 1 (AP1) SEQ ID NO:4; GSP3.G (SEQ ID NO:6.) and adaptor primer 1 (AP1) SEQ ID NO:4; and GSP5.P (SEQ ID NO:9) and adaptor primer 1 (AP1) SEQ ID NO:4. A diluted (1:50) aliquot of each of the primary PCR reactions is used as the input DNA for a nested round of PCR amplification in separate reactions with gene-specific primers (GSP2) of the secondary reaction, GSP2.II (SEQ ID NO:2), or GSP4.H (SEQ ID NO:7) or GSP6.Q (SEQ ID NO:10) and adaptor primer 2 (AP2) SEQ ID NO:5. The primers in the second PCR reaction have incorporated BglII/NcoI endonuclease restriction sites. The annealing temperatures of the GenomeWalker™ primary primer (AP1) and nested primer (AP2) are 59° C. and 71° C., respectively. Generally, gene specific primers are designed to have the following characteristics: 26-30 nucleotides in length, GC content of 40-60% with resulting temperatures for most of the gene specific primers in the high 60° C. range or about 70° C. The Taq polymerase used is Amplitaq Gold™, available through Perkin-Elmer Biosystems (Branchbury, N.J.). A number of temperature cycling instruments and reagent kits are commercially available for performing PCR experiments and include those available from PE Biosystems (Foster City, Calif.), Strategene (La Jolla, Calif.), and MJ Research Inc. (Watertown, Mass.). Any successful PCR conditions and methods can be used including but not limited to the modifications as described in Table 1. Following the primary PCR reaction, an aliquot is taken (10-15 μl) for agarose gel analysis. Isolation of each unknown sequence requires amplification from subgenomic libraries and a negative control (without DNA).

TABLE 1

PCR conditions
The PCR components and conditions generally used are outlined below:

| PRIMARY PCR (Method 1) | |
|---|---|
| Component | Amount/Volume required |
| Sub-library aliquot | 1 μl |
| Gene-specific primer | 1 μl (100 pmol) |
| Genome Walker ™ Adaptor primer 1 (AP1) | 1 μl |
| dNTP mix (10 mM of each dNTP) | 1 μl |
| DMSO | 2.5 μl (or 2-5% final concentration) |
| 10X PCR buffer (containing MgCl₂) | 5 μl (final concentration of 1X) |
| Amplitaq Gold ™ | 0.5 μl |
| Distilled Water | For final reaction volume of 50 μl |

Reaction Conditions for Primary PCR:

A. 9 minutes at 95° C.
B. 94° C. for 2 seconds, 70° C. for 3 minutes; repeat 94° C./70° C. cycling for total of 7 times
C. 94° C. for 2 seconds, 65° C. for 3 minutes; repeat 94° C./65° C. cycling for total of 36 times
D. 65° C. for 4 minutes as a final extension
E. 10° C. for an extended incubation

| NESTED PCR (secondary PCR reactions) | |
|---|---|
| Component | Amount/Volume Required |
| 1:50 dilution of the primary PCR reaction | 1 μl |
| Gene-specific primer | 1 μl (100 pmol) |
| GenomeWalker ™ Adaptor primer 2 | 1 μl |
| dNTP mix (10 mM of each dNTP) | 1 μl |
| DMSO | 2.5 μl |
| 10X PCR buffer (containing MgCl₂) | 5 μl (final concentration of 1X) |
| Amplitaq Gold ™ | 0.5 μl |
| Distilled water | to final reaction volume of 50 μl |

Reaction Conditions for Nested PCR:

A. 9 minutes at 95° C.
B. 94° C. for 2 seconds, 70° C. for 3 minutes; repeat 94° C./70° C. cycling for total of 5 times
C. 94° C. for 2 seconds, 65° C. for 3 minutes; repeat 94° C./65° C. cycling for total of 24 times
D. 65° C. for 4 minutes as a final extension
E. 10° C. for an extended incubation
MODIFICATION 1: Polymerase (Expand High Fidelity, Boehringer Mannheim, IN)
Primary PCR reaction step 1 95° C. 2 min
step 2 94° C. 2 sec
step 3 72° C. 3 min
step 4 repeat step 2 and 3, 7 times
step 5 94° C. 2 seconds
step 6 68° C. 3 minutes
step 7 repeat steps 5 and 6, 36 times
Secondary PCR reaction step 1, step 2, step 3 (same as primary PCR reaction)
step 4 repeat step 2 and 3, 5 times
step 5 and step 6 (same as primary PCR reaction)
step 7 repeat step 5 and step 6, 24 times TABLE 1-continued PCR conditions
The PCR components and conditions generally used are outlined below:

MODIFICATION 2: Polymerase (Amplitaq Gold ™, Perkin Elmer, Foster City, CA)
Primary PCR reaction step 1 95° C. 10 minutes
step 2 94° C. 2 seconds
step 3 70° C. 3 minutes
step 4 repeat step 2 and 3, 7 times
step 5 94° C. 2 seconds
step 6 68° C. 3 minutes
step 7 repeat step 5 and step 6, 24 times
MODIFICATION 3: Polymerase enzyme is Taq (Promega Corp., Madison, WI) same cycle conditions as Modification 2
except step 1 is 2 minutes.
MODIFICATION 4: Polymerase enzyme is AccuTaq (Sigma, St. Louis, MO) same cycle conditions as Modification 3.
MODIFICATION 5: Polymerase is Expand High Fidelity (BM)

| Mixture | Primary PCR | Secondary PCR |
| --- | --- | --- |
| 10X PCR buffer 2 | 2 µl | 1 µl |
| dNTP | 1 µl | 1 µl |
| adaptor primer (10 mM) | 1 µl AP1 | 1 µl AP2 |
| gene specific primer (10 mM) | 1 µl GSP1 | 1 µl GSP2 |
| Polymerase | 2.5 units | 3.5 units |
| template DNA | GenomeWalker ™ library 1 µl | 1:50 of primary PCR product |
| H20 | to 20 µl | to 50 µl |

Modification 5: PCR Cycling Conditions:

step 1 94° C. 1 minutes
step 2 94° C. 2 seconds
step 3 70° C. 3 minutes
step 4 repeat step 2 another 5 cycles
step 5 94° C. 2 seconds
step 6 68° C. 3 minutes
step 7 repeat step 5 another 34 cycles
step 8 68° C. 10 minutes
step 9 10° C. hold
MODIFICATION 6: PCR Conditions step 1 95° C. 2 minutes
step 2 94° C. 30 seconds
step 3 65° C. 30 seconds, decrease 1° C.
each cycle for 14 cycles
step 4 72° C. 3 minutes
step 5 repeat 2-4, 14 times
step 6 50° C.
step 7 72° C.
step 8 repeat 6-7, 15 times Those of skill in the art are aware of the variations in PCR conditions including choice of polymerase, cycling conditions and concentrations of the reaction components. Examples of other modifications to the above procedure include, but are not limited to the use of Expand High Fidelity polymerase (Boehringer Mannheim, Indianapolis, Ind.), Taq polymerase (Promega Corp., Madison, Wis.) and slight variations in temperature as described in Table 1.

Example 4

Promoter Isolation and Cloning

The DNA fragments resulting from the nested PCR amplification described in Example 3 are isolated and gel purified. A 40 µl aliquot of the secondary PCR is run on an agarose gel. The DNA fragment of the secondary PCR product is purified from the agarose gel using the BIO101 Geneclean II Kit (Midwest Scientific, Valley Park, Mo.) following the conditions suggested by the manufacturer. The purified DNA is digested with one or more restriction endonuclease(s) to permit ligation into a suitable cloning or expression vector. The promoter fragments are incorporated into a plant expression vector by positioning the Zea mays root promoter fragments in linkage with a reporter coding sequence by restriction enzyme digestion and ligation using methods known in the art (Sambrook et al., 1989). A suitable plant expression cassette comprises additional genetic components that enhance gene expression in plant cells, e.g., with maize cells, one can use the I-Zm.Hsp70, an intron of the maize heat shock protein as described in U.S. Pat. No. 5,593,874, herein incorporated by reference in its entirety; and the T-AGRTU.nos (T-nos, T-NOS 3'), a transcription termination signal from the nopaline synthase gene isolated from Agrobacterium tumefaciens. The purified DNA of the present invention is ligated as a BglII/SalI fragment into a construct that contains the necessary plant expression elements in operably linkage. An aliquot of the ligation reaction is transformed into a suitable E. coli host such as DH10B and the cells plated on selection medium (for DH10B, 100 µg/ml carbenicillin). Bacterial transformants are selected, grown in liquid culture, and the plasmid DNA isolated using a commercially available kit such as the Qiaprep Spin Microprep Kit (Qiagen Corp., Valencia, Calif.). Purified plasmid containing the predicted insert size are DNA sequenced in both directions using the dye terminator method and DNA primers homologous to the Zm.Hsp70 intron sequence and homologous to the vector sequence bordering the promoter insertion site. Additional primers are prepared based on the sequence produced from the first reaction and subsequent reactions. Restriction enzymes are available from a number of manufacturers (see for example, Boehringer Mannheim (Indianapolis, Ind.). The DNA sequences of the purified PCR product are identified as P-Zm.700102320 (SEQ ID NO:3), P-700203408 (SEQ ID NO:8) and P-700204518 (SEQ ID NO:11).

Example 5

Plant cell Analysis of Promoter Activity

Figure 2:
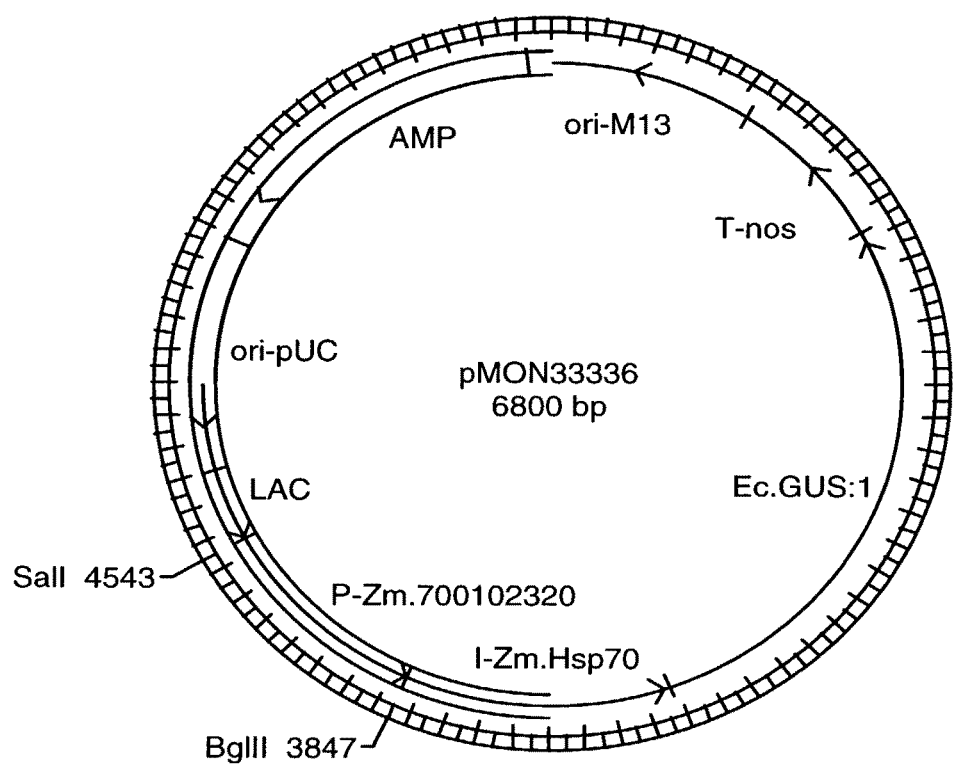
FIG. 2 is a plasmid map of pMON33336
Figure 3:
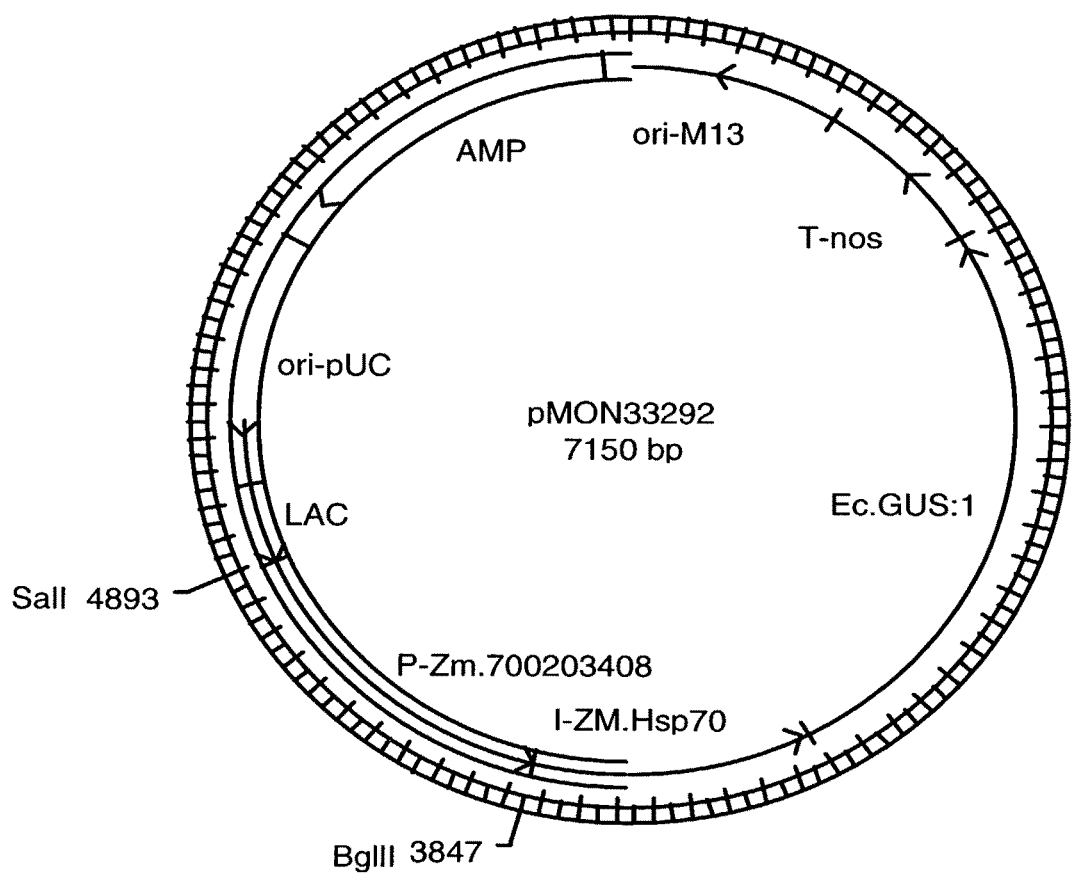
FIG. 3 is a plasmid map of pMON33292
Figure 4:
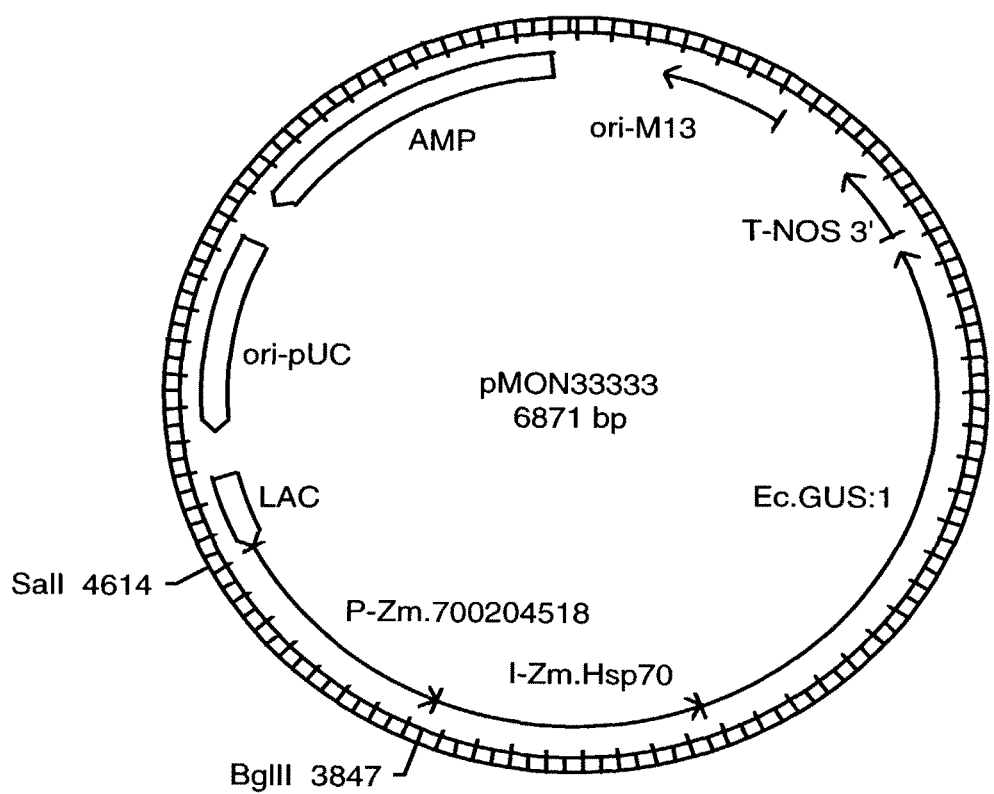
FIG. 4 is a plasmid map of pMON33333

The promoter fragments P-Zm.700102320, P-Zm.700204518 and P-Zm.700203408 are cloned into a plant expression cassette (pMON194690, FIG. 1) that expresses the Ec.GUS:1, a variant polynucleotide sequence of the reporter gene encoding β-glucuronidase for enhanced expression in plant cells (GUS, U.S. Pat. No. 5,859,347, herein incorporated by reference in its entirety). The resulting plant expression cassettes are contained in plasmids pMON33336 (P-Zm.700102320, FIG. 2), pMON33292 (P-Zm.700203408, FIG. 3), and pMON33333 (P-Zm.700204518, FIG. 4). The promoter DNA fragments of the present invention can replace the promoter elements of any plant expression construct to determine the promoter activity of the DNA fragments. Reporter coding sequences other than GUS can be used, such as luciferase (LUX) and green florescent protein (GFP), or any coding sequence for which an immunological or biochemical assay is available to detect or quantify the protein expressed.

The purified plasmid DNA of pMON33336, pMON33292, and pMON33333 are tested in a corn root and leaf protoplast electroporation assay for GUS activity relative to a CaMV 35S-GUS expression cassette (pMON 19469) used as a control. A number of assay methods for GUS expression are available and known to those of skill in the art as well as methods for preparation of leaf and root protoplasts.

A corn leaf protoplast isolation and electroporation protocol is followed essentially as described by Sheen, (Plant Cell 3:225-245, 1991, herein incorporated by reference in its entirely) with the following modifications: The seed used is FR27rhm X FRMo17rhm (Illinois Foundation Seeds, Champaign, Ill.). The seed is surface sterilized for 2 minutes in 95% ethanol, rinsed twice with sterile water, 30 minutes in 50% bleach (Clorox) plus 2 drops of Tween-20, three rinses in sterile water followed by a 5 minute soak in benlate/captan solution to prevent fungal growth. The seeds are germinated in phytotrays containing 100 milliliters ½ MS media (2.2 g/L MS salts, 0.25% gelrite), 8 seeds per phytotray. The seeds are grown 5 days at 26° C. in 16/8 hour day/night photoperiod and 7 days in the dark at 28° C. The second leaf from each plant is sliced longitudinally using Feather no. 11 surgical blades. Digestion time is two hours and 10 minutes in the light at 26° C. After digestion, the plates are swirled two times at 80-100 rpm for 20 seconds each and the protoplast/enzyme solution is pipetted through a 190 µm tissue collector. Protoplasts are counted using a hemacytometer counting only protoplasts that are intact and circular. Ten to fifty micrograms of DNA containing the vector of interest is added per cuvette.

Final protoplast densities at electroporation range from $3 \times 10^6$/ml to $4.5 \times 10^6$/ml. Electroporations are performed in the light using Bio-rad Gene puller cuvettes (Bio/Rad Hercules, Calif.) with a 0.4 cm gap and a maximum volume of 0.8 ml at 125 µfarads capacitance and 260 volts. The protoplasts are incubated on ice after resuspension in electroporation buffer and are kept on ice in cuvettes until 10 minutes after electroporation. The protoplasts are kept at room temperature for ten minutes before adding 7 milliliters of protoplast growth media. The protoplast culture media has been described (Fromm et al., Methods in Enzymology 153, 351-366, 1987). Culture plates are layered with growth media and 1.5% SeaPlaque agarose (FMC BioProducts, Rockland, Me.) to prevent protoplast loss. Samples are cultured in the light at 26° C., 16/8 day/night cycle, until harvested for the assay (typically 18-22 hours after electroporation). Samples are pipetted from the petri plates to 15 ml centrifuge tubes and harvested by centrifugation at 800-1000 rpm. The supernatant is removed and samples are assayed immediately for the gene of interest. Samples can also be frozen for later analysis.

Corn root protoplast isolation is performed using modifications to the protocol of Sheen et al. (The Plant Cell Vol. 3, 225-245, 1991). Seeds (FR27 X FRMo17, Illinois Foundation Seeds) are sterilized in a 500 ml sterile Corning storage bottle, polystyrene with a plug seal cap. Sterilization comprised covering the seeds with 95-100% ethanol for 2 minutes. The seeds are then rinsed twice with sterile distilled water. Two drops of Tween 20 are added to the bottle, and the seeds are then covered with 50% Clorox® bleach (sodium hypochlorite) and allowed to sit for 30 minutes. The seeds are then rinsed four times with sterile distilled water, treated with 0.25 tsp Orthocide® (Captan Garden Fungicide, Chevron Chemical Co., San Ramon, Calif.) and 1 tsp Benlate® (50% benomyl, 50% inert ingredients; E.I. du Pont de Nemours and Company Agricultural Products, Wilmington, Del.), covered with sterile distilled water, and allowed to sit for 5 minutes.

Seedlings are germinated, 8 per Phytatray II™, on ½ MS medium (2.2 g/L MS Basal Salts (M-5524), 2.5 g/L Phytagel™) at approximately 80 mL per Phytatray II™. The seedlings are germinated embryo side down for 4 days in the light (incubator at 26° C. with a 16 hr day/8 hr night cycle under cool white fluorescent bulbs, 10-25 µE).

After germination, the seedlings are pulled sideways from the phytatrays and then upwards to minimize the amount of media removed with the roots. Large main roots are removed by cutting at the base of the seed with a blade. The tissue is then wounded with a triple-bladed scalpel (three scalpels bond together in parallel) at an angle of 45 degrees to the direction of root length. The wounds are made perpendicular to the direction of growth and the segments about 2-4 mm in length.

Six to seven grams of wounded material is placed in a deep petri dish (100×25 mm) that contains 40 ml of enzyme mix (1.5% cellulase YC, 0.1% Pectolyase, 0.7 M mannitol, 10 mM MES (2-[N-morpholino]ethanesulfonic acid), 1 mM $CaCl_2$, 1 mM $MgCl_2$, 0.1% bovine serum albumin (BSA), and 17 mM Beta-mercaptoethanol; pH 5.7). The petri dish with enzyme and root tissue is then vacuum infiltrated for 30 seconds.

Digestion is performed in the light (cool white fluorescent bulbs, 10-25 µE) for 135 minutes at 50 rpm on an Orbit™ platform shaker at 26° C. After digestion, plates are swirled by hand at about 100 rpm for 50 seconds to release protoplasts from the tissue mass. Protoplasts are separated out by straining the enzyme mix through a sieving assembly. The sieving assembly consists of one collector with a wide mesh (Bellco Glass, Inc. Cat #1985-00030) that is placed inside of another collector with a 190 µm sieve. The sieved protoplasts are transferred to a 50 mL conical bottom centrifuge tube, and pelleted by centrifugation at 200×g for 8 minutes. The pellet is resuspended in 10 mL of rinse media (0.7 M mannitol, 4 mM MES (pH 5.7), pH 5.7) and centrifuged again at 200×g for 8 minutes.

The pellet is then resuspended in 10 mL of electroporation buffer (0.7 M mannitol, 4 mM MES, 1.0 mM Beta-mercaptoethanol, 25 mM KCl, pH 5.7), the protoplasts are counted with a Hausser Scientific Bright-Line™ hemacytometer. The protoplasts are then pelleted again and resuspended in electroporation buffer at a density of $0.5 \times 10^6$ cells/mL.

In preparation for transfection, 750 µl of protoplasts at $0.5 \times 10^6$ cells/mL are added to each BioRad Gene Pulser® cuvette (0.4 cm gap) followed by the addition of DNA. Transfection is performed by electroporation at 125 µF and 250 V on a BioRad Gene Pulser™ Model No. 1652076, BioRad Capacitance Extender Model No. 1652087. Prior to and post transfection the cuvettes are placed on ice for 10 minutes. The protoplasts and DNA are mixed by inverting the cuvettes twice immediately prior to electroporation.

After transfection, protoplasts are poured into agarose layered plates (MS Fromm+0.7 M mannitol+15 g/L SeaPlaque® agarose (FMC® Bioproducts)) in 3.5 mL of MS Fromm+0.7 M mannitol (4.4 g/L MS salts (Gibco, 500-1117EH), 1 mL/L 1000× vitamins (1.3 g/L nicotinic acid, 250 mg/L thiamine HCl, 250 mg/L pyridoxine HCl, 250 mg/L calcium panthothenate), 20 g/L sucrose, 2 mg/L 2,4-D, 0.1 g/L inositol (myo-inositol), 0.13 g/L asparagine, 127 g/L mannitol) and cultured overnight. All chemicals used are obtained from Sigma Chemical Company, St. Louis, Mo., except as indicated. This overnight culture is performed in an incubator at 26° C. with a 16 hr day/8 hr night cycle utilizing cool white fluorescent bulbs, 10-25 µE.

Protoplasts are harvested after one day; culture time is 18-22 hr. Protoplasts are removed from the plate using a 10 mL serological pipette, with care taken not to draw up the agarose layering. Protoplasts are then put in 15 mL conical bottom centrifuge tubes and centrifuged at 200×g for 8 minutes. The supernatant is removed and the pellets are placed immediately on dry ice. All pellets are then stored in a −80° C. freezer until assayed.

The expression of GUS by the corn root promoters is measured as a percentage of the activity observed when pMON 19469 is set to 100. The test constructs are electroporated into corn leaf and root protoplasts and replicated 2 or 4 times as shown in Table 2. The assay is performed by the MUG method that provides a quantitative analysis of the GUS expression in the transgenic plant cells. Total protein is extracted from each sample, measured and concentration adjusted such that each sample contains the same amount of total protein. Total protein is assayed using Bio-Rad Protein Assay kit. Serial dilutions of BSA protein from 0.05 mg/ml to 0.5 mg/ml are used for the standard curve. The MUG assay uses 500 µl of GUS extraction buffer added to the tissues, and tissues are ground with a teflon pestle in 1.5 ml eppendorf tube and centrifuged at 10K RPM for 5 minutes at 4° C. (Beckman GS-15R). Four hundred µl of supernatant is transferred to a fresh 96-deep well plate. The extracts are frozen on dry ice, then stored at −80° C. until use. The MUG assay consisted of generating a standard curve of activity with a serial dilution of 4-methyl umbelliferone (Sigma Chemical Co Cat#M1381, St Louis, Mo.) from 31.2 pmoles to 2000 pmoles. Five µl of each extract is added to a flat bottom 96-well plate (Falcon #3872, BD Biosciences) in duplicate after the plate is read for blanking the background. Two hundred µl of GUS assay solution (0.1M $KPO_4$ pH7.8, 1.0 mM EDTA, 5% glycerol, 10.0 mM DTT, 2 mM 4-methyl umbelliferyl glucuronide, Fluka #69602) is added to each well and mixed with the samples by pipetting. The Plate is read kinetically on a F-max (Molecular Devices, Sunnyvale Calif.) at 37° C. with the filter pair: excitation-355/emission-460. A typical read consists of 21 readings at 3 minute intervals. GUS activity (pmol/min/mg protein) is calculated base on MUG results and protein results of each sample. 1.5 µl of extracts is added to flat bottom 96-well plate (Falcon) in duplicate. 200 ul of diluted dye reagent is added and mixed with the samples. The absorbance at 595 nm is measured in Spectromax 250 (Molecular Devices, Sunnyvale Calif.) at room temperature after 5 minutes incubation at room temperature.

A control plasmid (Luc plasmid) containing the plant expression cassette for CaMV.35S/Luc/T-nos is co-electroporated to standardize the electroporation experiments. The same amount of the Luc plasmid is added to each solution with the test constructs and electoporated. A sample of the electroporated cells are assayed for luciferase activity after each test. Quantitative luciferase assays is performed as follows: 50 µl of extract is added to a cuvette containing 0.2 mls of 25 mM Tricine pH7.8, 15 mM $MgCl_2$, 5 mM ATP, and 0.5 mg/ml BSA. 0.5 mM luciferin substrate is automatically dispensed by the luminometer (Berthold Bioluminat LB9500C) and the peak luminescence measured during a 10 second count at 25° C. Three to ten reactions are run per sample. The values shown in table 2 have been normalized to have equivalent Luc expression in each sample.

Example 6

Figure 6:
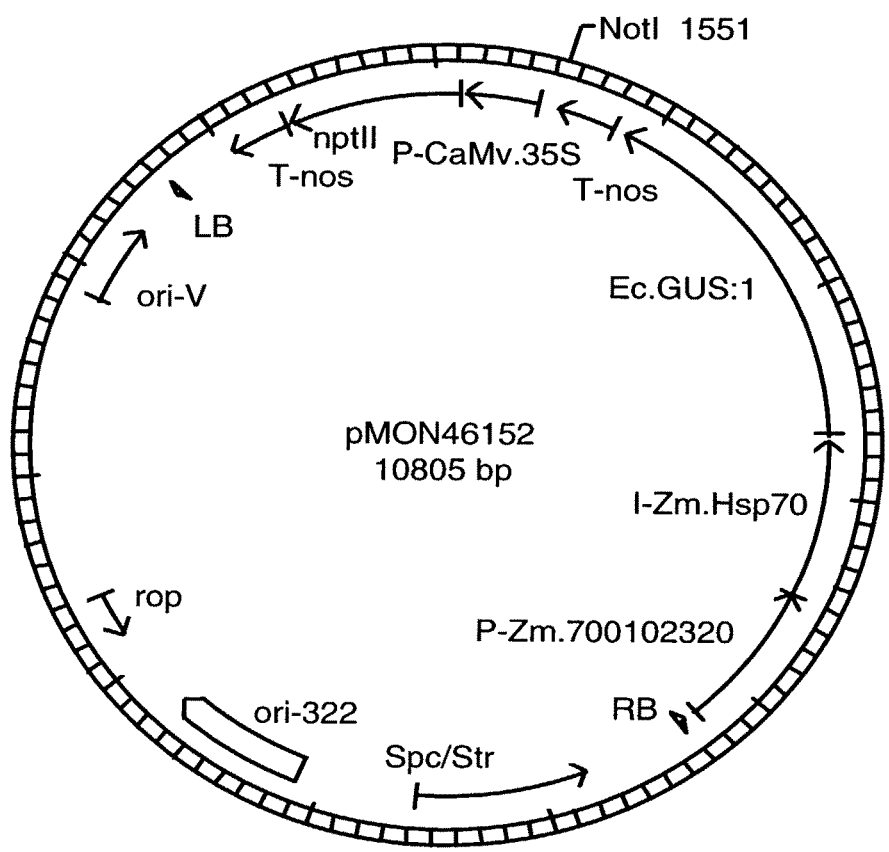
FIG. 6 is a plasmid map of pMON46152
Figure 7:
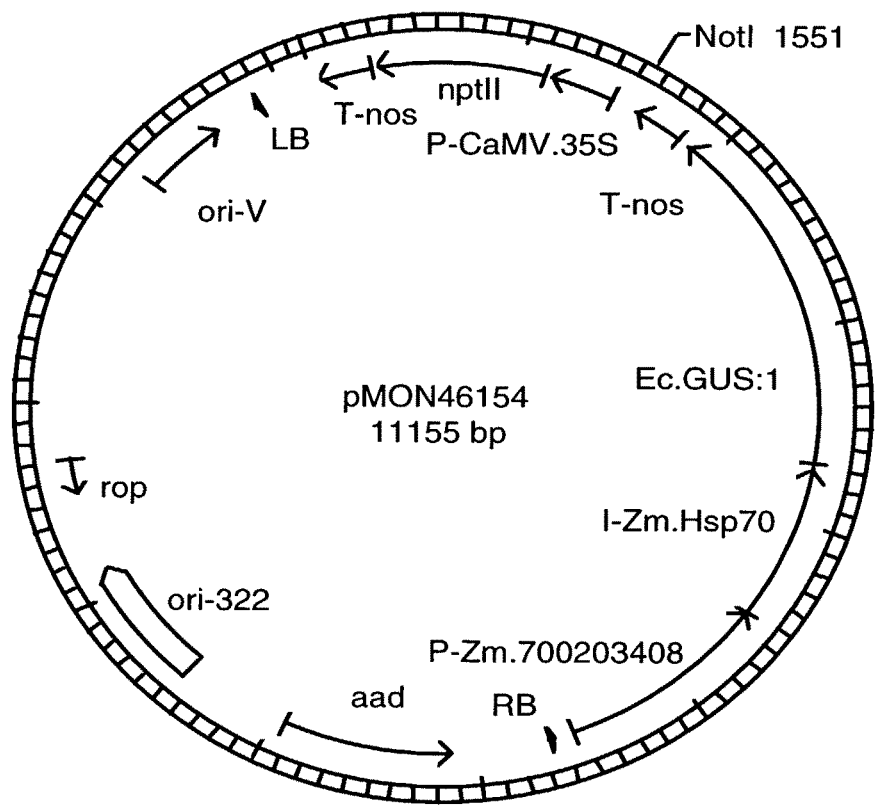
FIG. 7 is a plasmid map of pMON46154
Figure 8:
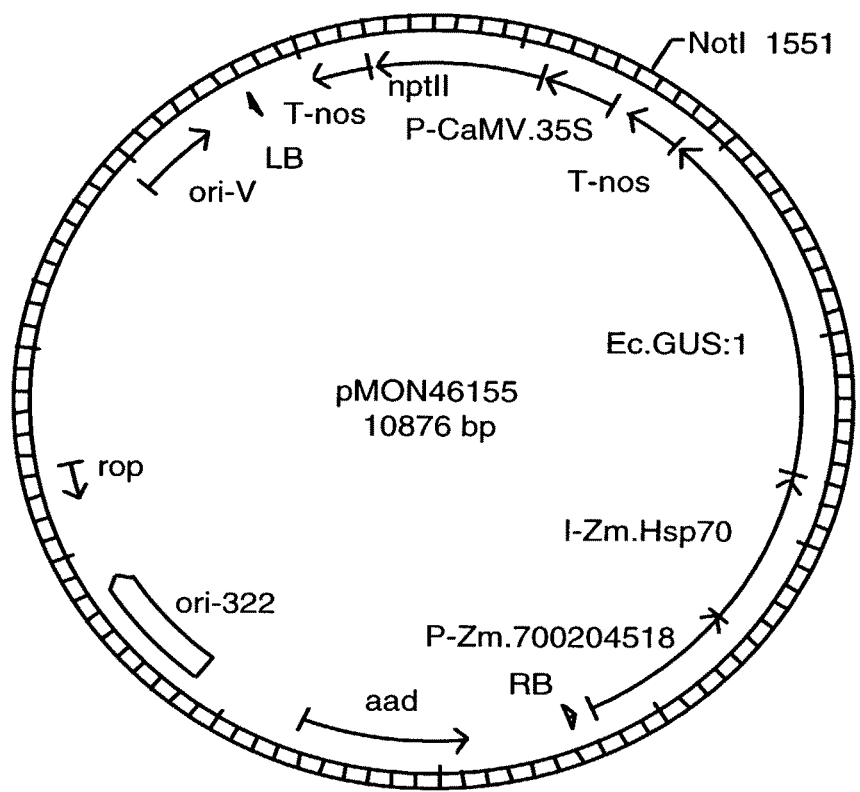
FIG. 8 is a plasmid map of pMON46155

DNA constructs are made for plant transformation by the addition of a selectable marker expression cassette. The promoter DNA fragments of P-Zm.700102320 (SEQ ID NO:3), P-Zm.700203408 (SEQ ID NO:8) and P-Zm.700204518 (SEQ ID NO:11) are ligated into a plant expression cassette containing the genetic elements for expression of GUS in monocot plants. The construct pMON46152 (FIG. 6) is constructed to link the P-Zm.700102320/1-Hsp70/Ec.GUS:1/T-nos together in an expression cassette and to contain the P-CaMV.35S/nptII/T-nos expression cassette in the same T-DNA for selection of transgenic corn plants on paramomycin. pMON46154 (FIG. 7) and pMON46155 (FIG. 8) are constructed in the same manner as pMON46152. As a comparative expression cassette, pMON 18365 containing the same GUS reporter gene, is transformed in the same experiment with the root promoter constructs.

Transgenic corn plants can be produced by an *Agrobacterium* mediated transformation method using the DNA constructs of the present invention. DNA constructs useful in plant transformation methods mediated by *Agrobacterium* contain a binary construct that has one or more *Agrobacterium* Ti plasmid border elements, left border (LB), Right Border (RB), plasmid maintenance elements (ORI-322, ori-V, ROP), bacteria selectable marker genes, e.g., aad, providing resistance to spectinomycin and streptomycin (SPC/STR). A disarmed *Agrobacterium* strain C58 (ABI) harboring a binary vector of the present invention is used for all the experiments. The DNA construct is transferred into *Agrobacterium* by a triparental mating method (Ditta et al., Proc. Natl. Acad. Sci. 77:7347-7351). Liquid cultures of *Agrobacterium* are initiated from glycerol stocks or from a freshly streaked plate and grown overnight at 26° C.-28° C. with shaking (approximately 150 rpm) to mid-log growth phase in liquid LB medium, pH 7.0 containing 50 mg/l kanamycin, 50 mg/l streptomycin and spectinomycin and 25 mg/l chloramphenicol with 200 µM acetosyringone (AS). The *Agrobacterium* cells are resuspended in the inoculation medium (liquid CM4C) and the density is adjusted to $OD_{660}$ of 1. Corn embryos are dissected directly into the *Agrobacterium* solution with OD around 1.0 in ½ MSPL plus 200 µM acetosyringone and let sit for 5 to 10 minutes. The solution is decanted into the center of the co-culture plates and the *Agrobacterium* liquid is removed. Embryos are placed scutellum side up. Co-culture for 1 day at 23° C. in the dark. Before placing on selection, embryos are placed on delay culture (MS basal media (Murashige et al., Physiol. Plant 15:473-497, 1962) containing 0.5 mg/L 2,4-D, 2.2 mg/L picloram, 500 mg/L carbenicillin, 20 µM silver nitrate) for 3 days. Embryos are then placed on selection media (MS basal media containing 0.5 mg/L 2,4-D, 2.2 mg/L picloram, 500 mg/L

TABLE 2

Corn protoplast analysis of corn root promoter sequences driving expression of GUS:1

|   | Promoter DNA | pMON | Root Protoplast | Leaf protoplast | Root/leaf ratio |
|---|---|---|---|---|---|
| 1 | CaMV 35S | 19469 | 100 | 100 | 1 |
| 2 | P-Zm.700203408 | 33292 | 70, 99 | 28, 32, 56, 41 | 84.5/39.2 = 2.1 |
| 3 | P-Zm.700204518 | 33333 | 36, 28, 48, 46 | 19, 18, 17, 17 | 39.5/17.7 = 2.2 |
| 4 | P-Zm.700102320 | 33336 | 23, 44 | 2, 2, 2, 2 | 33.5/2 = 16.7 |

The analysis of the root promoter DNA sequences shows that P-Zm.700102320 is highly enhanced for expression in root cells relative to leaf cells with a ratio of 16.7. Although, the relative expression level of GUS driving by the P-Zm.700102320 promoter in root cells is about one third of that observed for the CaMV 35S promoter, the extremely low leaf protoplast expression makes this promoters desirable for use to direct differential expression in a transgenic plant.

carbenicillin, 20 μM silver nitrate, and 50 mg/L paromomycin) for 2 weeks. After 2 weeks, all visible coleoptiles are removed and embryos are transferred to a second regeneration media (MS basal media containing 0.5 mg/L 2,4-D, 2.2 mg/L picloram, 500 mg/L carbenicillin, 20 μM silver nitrate, and 100 mg/L paromomycin) for 2 weeks. The embryos are subcultured on the same medium 2 additional times with a 2-week transfer cycle. All previous steps from delay through selection occur at 27° C. in the dark. Callus events consisting of healthy type I tissue are transferred to MS basal medium containing 6BA for 5 to 7 days in the light at 27° C. After the BA pulse, the events are transferred to MSOD plates with 100 mg/L paromomycin for 4 to 5 weeks. As plants emerged, they are transferred to a covered container containing the same medium for rooting. Rooted plants are transferred to soil in pots.

Example 7

Figure 5:
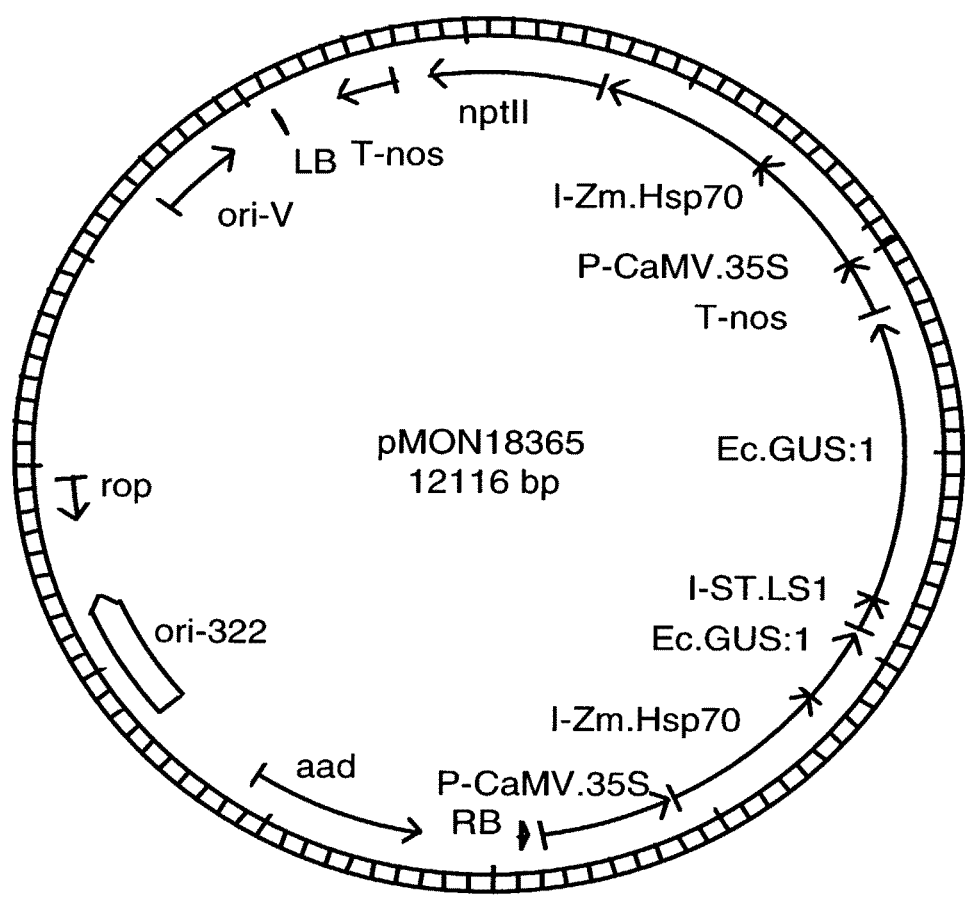
FIG. 5 is a plasmid map of pMON18365
Figure 9:
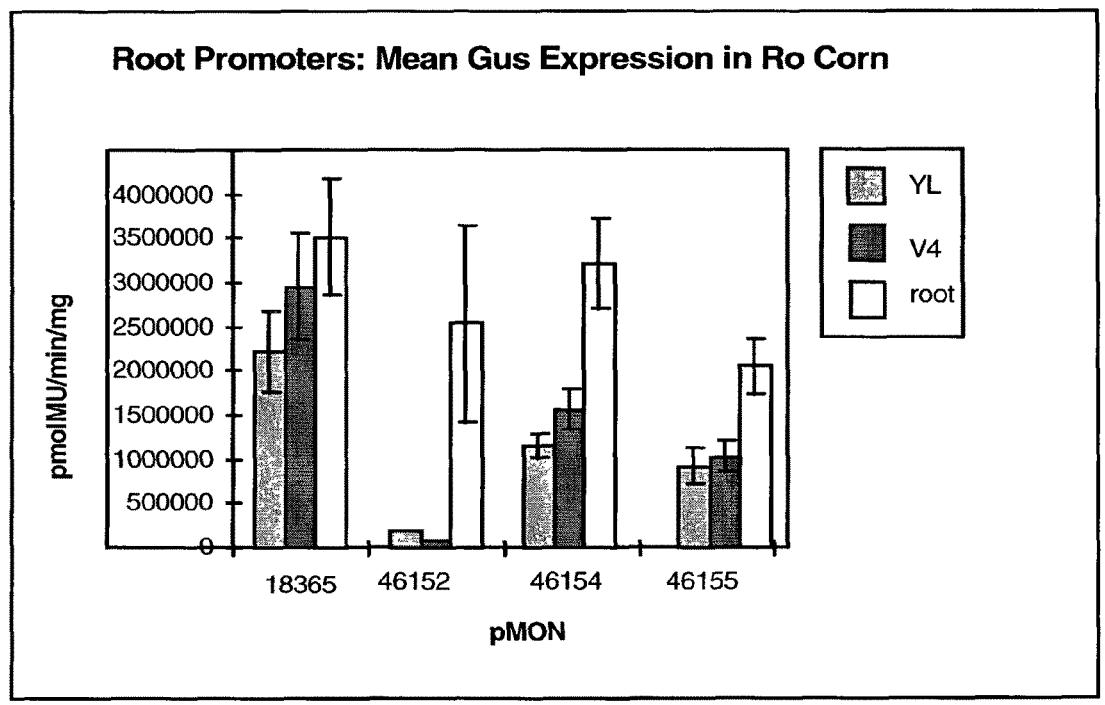
FIG. 9 is a graph of the reporter gene (GUS) expression analysis performed on young leaves (newly emerged), fourth surviving leaf from base of the plant, and root tissues of $R_0$ corn plants transformed with control constructs and pMON46152 containing the root enhanced promoter of the present invention.

Transgenic corn plants transformed with the DNA constructs pMON 18365 (FIG. 5), pMON46152 (FIG. 6), pMON46154 (FIG. 7) and pMON46155 (FIG. 8) are growth in pots in a greenhouse. These plants are assayed for GUS expression using the MUG assay as described in the analysis of the protoplasts (EXAMPLE 5). Tissue samples are collected from the newest emerged leaf (referred herein as YL, the young leaf) at a growth stage later than V8, the fourth surviving leaf from the plant base V4, and the root. The results of the GUS analysis of these lines and tissues as illustrated in FIG. 9. For pMON18365, the CaMV 35S promoter is driving the expression of the GUS gene that contains the potato LS1 intron (I-St.LS1), sixteen transgenic lines are assayed for expression of GUS expressed in pmol/MU/min/mg, the young leaf (YL) samples show a mean of 2,225,878, the V4 leaf samples show a mean of 2,954,229, and the root samples show a mean of 3,517,380. For pMON46152, the P-Zm.700102320 promoter is driving the expression of the GUS gene, seventeen transgenic lines are assayed for expression of GUS expressed in pmol/MU/min/mg, the young leaf (YL) samples show a mean of 175,802, the V4 leaf samples show a mean of 70,642, and the root samples show a mean of 2,542,226. For pMON46154, the P-Zm.700203408 promoter is driving the expression of the GUS gene, fifteen transgenic lines are assayed for expression of GUS expressed in pmol/MU/min/mg, the young leaf (YL) samples show a mean of 1,148,794, the V4 leaf samples show a mean of 1,559,493, and the root samples show a mean of 3,210,164. For pMON46155, the P-Zm.700204518 promoter is driving the expression of the GUS gene, fifteen transgenic lines are assayed for expression of GUS expressed in pmol/MU/min/mg, the young leaf (YL) samples show a mean of 911,996, the V4 leaf samples show a mean of 1,025,446, and the root samples show a mean of 2,056,952 (FIG. 9).

The P-Zm.700102320 promoter demonstrates that in whole plants it provides enhanced expression of a transgene product in root tissues relative to leaf tissues. The ratio of root/leaf expression is between 14 and 36 fold enhancement. In the same experiment, other root promoters P-Zm.700203408 and P-Zm.700204518 only demonstrate root/leaf ratios between 2 and 3 fold difference.

Example 8

Figure 10:
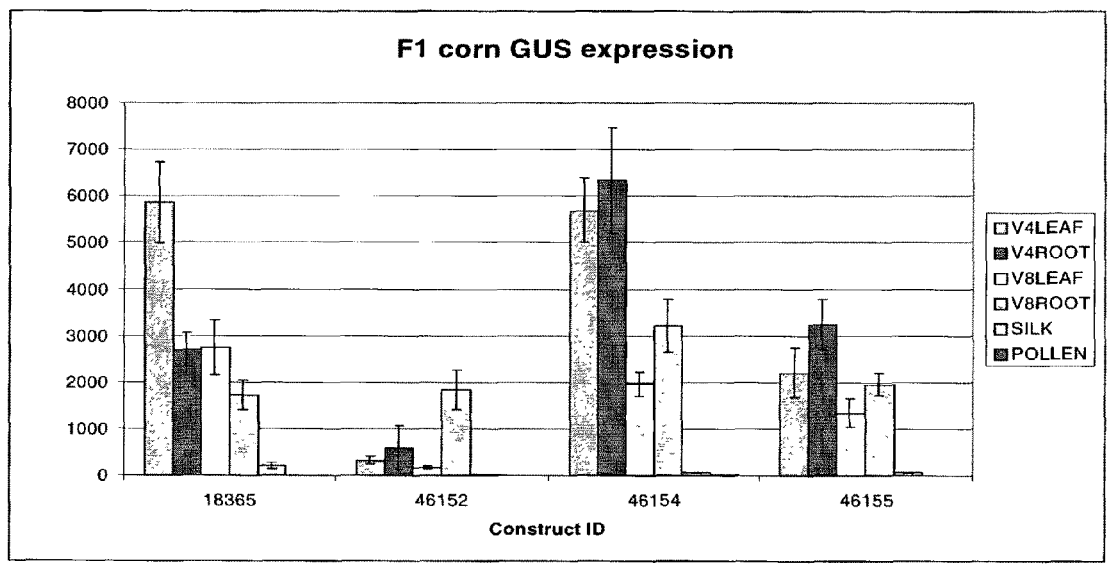
FIG. 10 is a graph of the reporter gene (GUS) expression analysis performed on six to tissues of $R_1$ corn plants transformed with constructs pMON18365, pMON46152, pMON46154, and pMON46155.

The transgenic corn plants containing the root enhanced promoter constructs are analyzed for GUS expression in the $F_1$ generation progeny. Ten events from each construct (pMON46152, pMON46154, pMON46155 and pMON18365) and 3 plants/event are selected for analysis of gene expression levels in various plant tissues. Tissues that are sampled in this study include root and youngest leaf at V4 and V8 stage, and pollen and silk. A summary of the expression data is shown in FIG. 10 for the six tissues that are quantitatively examined. The root expression for all three promoters is greater than or about the same as the control construct pMON18365 that contains the CaMV 35S promoter. The promoter, (P-Zm.700102320 (pMON46152) shows the lowest level of expression in leaf tissue. The promoter, P-Zm700203408 (pMON46154) demonstrates the highest overall expression in leaves and roots, however root expression is enhanced relative to the CaMV 35S promoter although GUS expression is detectable in pollen. P-Zm.700204518 (pMON46155) resembles the expression pattern observed in the tissues of transgenic plants containing pMON46154, except the overall expression level is reduced. This construct and pMON46152 does not show any GUS expression in pollen using the quantitative enzyme activity assay, but faint staining could be seen following histochemical staining.

Example 9

Promoters that enhance the expression of transgenes in root cells and root tissues are especially useful for the expression of proteins toxic to root pests. Of particular interest is the expression of insecticidal proteins toxic to the corn rootworm (*Diabrotica* spp.). Insecticidal protein genes isolated from *Bacillus thuringiensis*, e.g. ET8076 (WO 0066742, herein incorporated in its entirely), cry3Bb gene (WO 9931248, herein incorporated in its entirely), ET70 (WO 0026378, herein incorporated in its entirely), and PS149B1 (Moellenbeck, et al. 2001. Nature Biotech 19:668-672, herein incorporated in its entirely), have been shown to be toxic to the corn root worm. The enhanced expression of the gene sequences encoding these proteins in the roots of corn plants relative to other plant cells or tissues, reduces the potential exposure that nontarget organisms may receive of the expressed protein in the environment.

Figure 11:
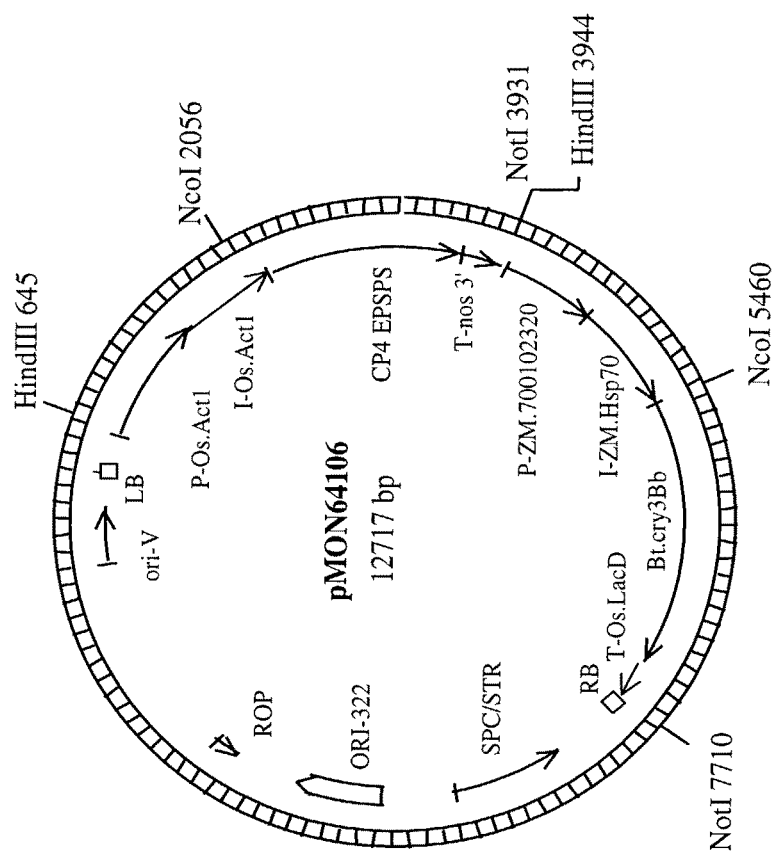
FIG. 11 is a plasmid map of pMON64106
Figure 12:
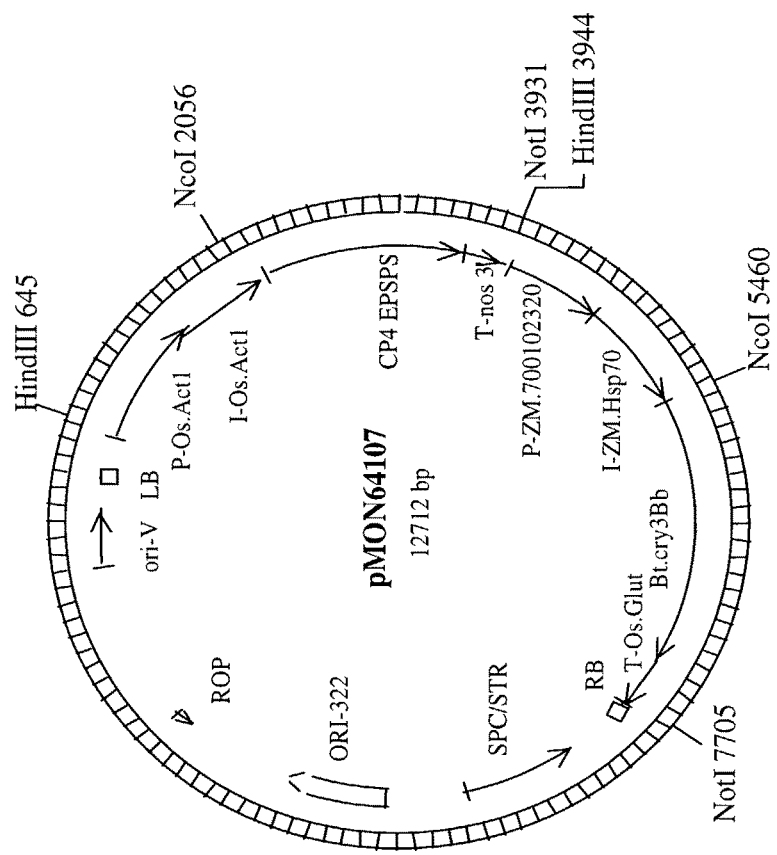
FIG. 12 is a plasmid map of pMON64107
Figure 13:
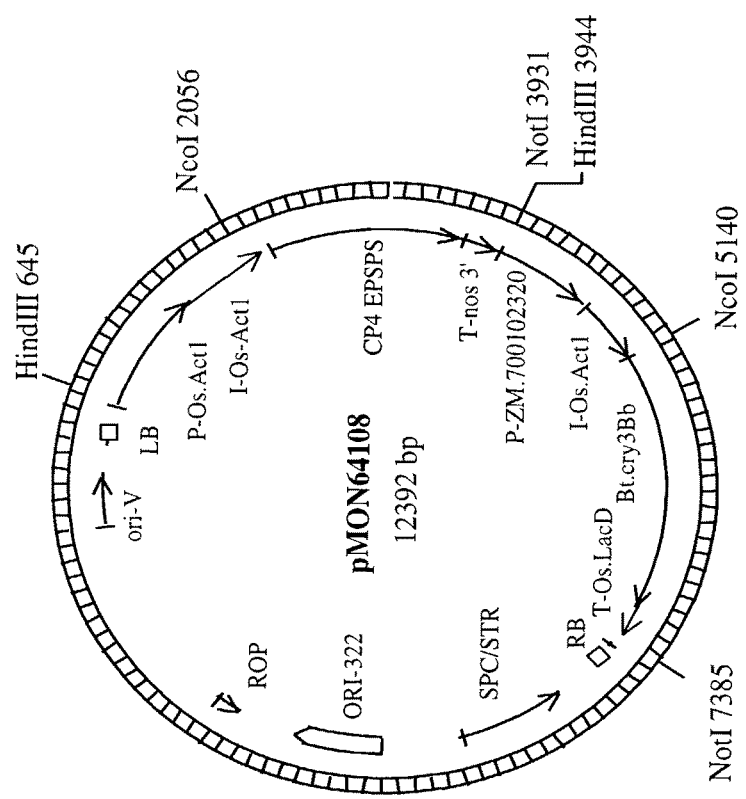
FIG. 13 is a plasmid map of pMON64108
Figure 14:
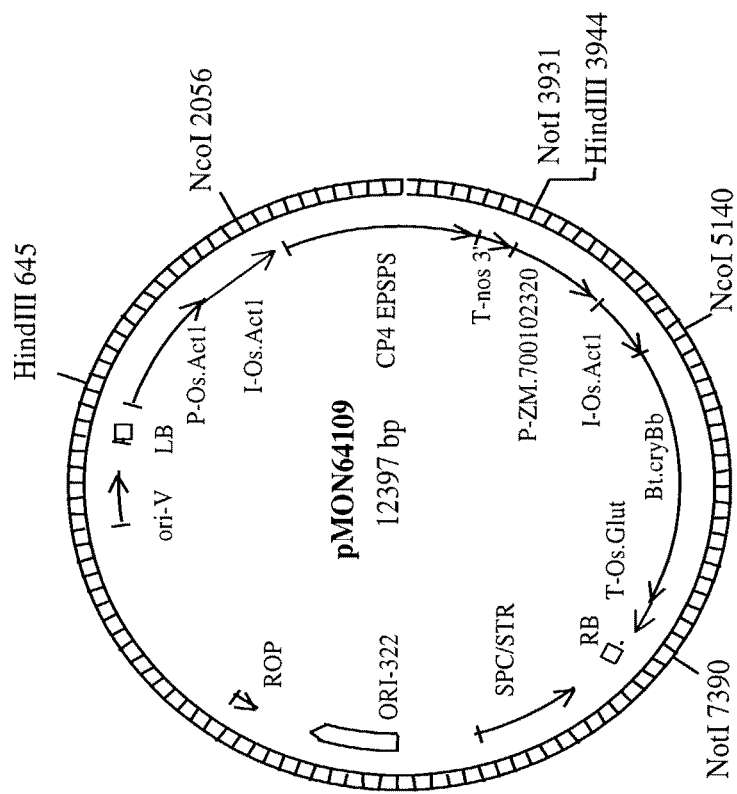
FIG. 14 is a plasmid map of pMON64109

DNA constructs that contain the P-ZM.700102320 promoter linked to the DNA molecule encoding the CRY3Bb protein are assembled in combination with other genetic elements that contribute to higher expression levels by enhancing the stability or translatability of the transcribed mRNA. Some examples include, but are not limited to the expression cassettes contained in pMON64106 (FIG. 11) the cassette P-Zm.700102320/I-Zm.Hsp70/cry3Bb/T-Os.LacD, pMON64107 (FIG. 12) that contains the cassette P-Zm.700102320/I-Zm.Hsp70/cry3Bb/T-Os.Glut, pMON64108 (FIG. 13) that contains the cassette P-Zm.700102320/1-Os.Act1/cry3Bb/T-Os.LacD, and pMON64109 (FIG. 14) that contains the plant expression cassette P-Zm.700102320/I-Os.Act1/cry3Bb/T-Os.Glut. Transformation of these DNA constructs into corn cells and analysis of the regenerated corn plants is shown in table 3. Root and leaf tissue is assayed for the CRY3Bb protein (ppm) by ELISA from V4 and V8 corn growth stages. The effect of intron and 3' UTR regulatory elements on the expression levels in each of the tissues is measured. All of the combinations of regulatory elements with the P-Zm.700102320 promoter demonstrate a high root to leaf ratio of the insecticidal protein.

Additional plant expression cassettes can be included in the T-DNA of the DNA construct or in a different T-DNA residing on the same construct, these can include, but are not limited to the T-Os.Lacd (lactate dehydrogenase 3' UTR, WO 200011200, herein incorporated by reference in its entirety) and the T-Os.Glut (glutelin 3' UTR from rice, WO 200011200, herein incorporated by reference in its entirety). These additional expression cassettes can include selectable marker genes, e.g. the aroA:CP4 gene (CP4 EPSPS, U.S. Pat. No. 5,633,435) encoding a glyphosate resistant enzyme and nptII encoding neomycin phosphotransferase, as well as other genes of agronomic importance.

TABLE 3

Root to leaf Bt CRYSBb protein expression (ppm) in V4 and V8 corn

| | INTRON | 3' UTR | V4 root | V4 leaf | V4 root/leaf | V8 root | V8 leaf | V8 root/leaf |
|---|---|---|---|---|---|---|---|---|
| pMON64106 | Hsp70 | Os Lacd | 9.83 | 0.00 | NA | 0.17 | 0.00 | NA |
| pMON64107 | Hsp70 | Os Glut | 12.67 | 0.40 | 31.68 | 2.67 | 0.00 | NA |
| pMON64108 | Os Act | Os Lacd | 13.67 | 0.42 | 32.55 | 8.83 | 0.53 | 16.66 |
| pMON64109 | Os Act | Os Glut | 11.17 | 0.45 | 24.82 | 3.67 | 0.82 | 4.48 |

Example 10

Identification of Cis Acting Elements

Cis acting regulatory elements necessary for proper promoter regulation can be identified by a number of means. In one method, deletion analysis is carried out to remove regions of the promoter and the resulting promoter fragments are assayed for promoter activity. DNA fragments that are considered necessary for promoter regulation if the activity of the truncated promoter is altered compared to the original promoter fragment. Through this deletion analysis, small regions of DNA can be identified that are necessary for positive or negative regulation of transcription. Promoter sequence motifs can also be identified and novel promoters engineered to contain these cis elements for modulating expression of operably linked transcribable sequences. See for example U.S. Pat. No. 5,223,419, herein incorporated by reference in its entirety, U.S. Pat. No. 4,990,607 herein incorporated by reference in its entirety, and U.S. Pat. No. 5,097,025 herein incorporated by reference in its entirety.

An alternative approach is to look for similar sequences between promoters with similar expression profiles. Promoters with overlapping patterns of activity can have common regulatory mechanisms. Several computer programs can be used to identify conserved, sequence motifs between promoters, including but not limited to MEME, SIGNAL SCAN, or GENE SCAN. These motifs can represent binding sites for transcriptions factors that act to regulate the promoters. Once the sequence motifs are identified, their function can be assayed. For example, the motif sequences can be deleted from the promoter to determine if the motif is necessary for proper promoter function. Alternatively, the cis element motif can be added to a minimal promoter to test whether it is sufficient to activate or enhance transcription in certain plant cells or tissues. In the present invention, a region of DNA polynucleotide sequence of SEQ ID NO:3 from position 110-192 and a DNA polynucleotide sequence at least 90% homologous to this sequence or a motif sequence of DNA polynucleotide sequence of SEQ ID NO:3 from position 126-164 and a DNA polynucleotide sequence at least 90% homologous can be assayed for root cell and tissue transcription enhancement of transgenes. Suspected negative regulatory elements can be tested for sufficiency by combining with an active promoter molecule and testing for a reduction in promoter activity. Some cis acting regulatory elements may require other elements to function. Therefore, multiple elements can be tested in various combinations by any number of methods known to those of skill in the art.

Once functional promoter elements have been identified, promoter elements can be modified at the nucleotide level to affect protein binding. The modifications can cause either higher or lower affinity binding that would affect the level of transcription from that promoter.

Promoter elements can act additively or synergistically to affect promoter activity. In this regard, promoter elements from different 5' regulatory regions can be placed in tandem to obtain a promoter with a different spectrum of activity or different expression profile. Accordingly, combinations of promoter elements from heterologous sources or duplication of similar elements or the same element can confer a higher level of expression of operably linked transcribable sequences. For example, a promoter element can be multimerized to increase levels of expression specifically in the pattern affected by that promoter element. Novel cis acting elements can be combined to create chimeric DNA molecules with promoter activity. The cis elements of the promoter DNA molecule of the present invention can be combined with other promoter DNA molecules that may be deficient in expression in root cells and root tissues to enhance their activity in these cells and tissues, e.g. various tissue specific elements of the CaMV 35S promoter (U.S. Pat. Nos. 5,097,025, and 5,110,732, herein incorporated by reference in their entirety).

Additionally, the cis elements of the present invention can be combined with other known root cell and root tissue cis elements to create a novel promoter DNA molecule with enhanced root expression, e.g. the root expression element AS-1 of the CaMV 35S promoter (U.S. Pat. No. 5,023,179, herein incorporated by reference in its entirety).

The technical methods needed for constructing chimeric DNA molecules in expression vectors containing the novel engineered 5' regulatory elements are known to those of skill in the art. The engineered promoters are tested in expression vectors and tested transiently by operably linking the novel promoters to a suitable reporter gene, such as GUS, and testing in a transient plant assay. The novel promoters are operably linked to one or more genes of interest and incorporated into a plant transformation vector along with one or more additional regulatory elements and transformed into a target plant of interest by a suitable DNA delivery system. The stably transformed plants and subsequent progeny are evaluated by any number of molecular, immunodiagnostic, biochemical, phenotypic, or field methods suitable for assessing the desired agronomic characteristic(s).

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application is specifically and individually indicated to be incorporated by reference.

We claim:

1. A DNA molecule comprising a regulatory element selected from the group consisting of:
   (a) a nucleic acid sequence comprising SEQ ID NO:3;
   (b) a nucleic acid sequence comprising a fragment of SEQ ID NO:3 that enhances expression in root tissue relative to leaf tissue; and
   (c) a nucleic acid sequence comprising at least 95% identity to SEQ ID NO:3 that enhances expression in root tissue relative to leaf tissue, wherein the DNA molecule is operably linked to a heterologous transcribable polynucleotide.

2. A DNA molecule of claim 1, operably linked to a 3' transcription termination DNA polynucleotide.

3. The DNA molecule of claim 1, wherein said heterologous transcribable polynucleotide is transcribed into a RNA molecule that encodes a protein.

4. The DNA molecule of claim 1, wherein said heterologous transcribable polynucleotide is transcribed into a RNA molecule that does not encode a protein.

5. An isolated DNA molecule comprising SEQ ID NO:3.

6. A transgenic plant made by a method comprising the steps of:
   (i) introducing into the genome of a plant cell the DNA molecule of claim 1; and (ii) selecting said transgenic plant cell; and
(iii) regenerating said transgenic plant cell into a transgenic plant.

7. The transgenic plant of claim 6, wherein said DNA molecule confers disease resistance to said transgenic plant.

8. The transgenic plant of claim 6, wherein said DNA molecule confers enhanced root growth to said transgenic plant.

9. The transgenic plant of claim 6, wherein said DNA molecule confers insect resistance to said transgenic plant.

10. The transgenic plant of claim 6, wherein said DNA molecule confers herbicide tolerance to said transgenic plant.

11. The transgenic plant of claim 6, wherein said DNA molecule confers stress tolerance to said transgenic plant.

12. A seed of said transgenic plant of claim 6.

13. The DNA molecule of claim 1, wherein said nucleic acid sequence is at least 95% identical to SEQ ID NO:3.

14. The DNA molecule of claim 1, wherein said nucleic acid sequence is set forth in SEQ ID NO:3.

15. The transgenic plant of claim 6, wherein said DNA molecule is operably linked to a 3' transcription termination DNA polynucleotide.

\* \* \* \* \*